(12) United States Patent
Wood et al.

(10) Patent No.: US 11,633,442 B2
(45) Date of Patent: Apr. 25, 2023

(54) METHODS FOR COMBINING ADOPTIVE T CELL THERAPY WITH ONCOLYTIC VIRUS ADJUNCT THERAPY

(71) Applicant: TVAX BIOMEDICAL I, LLC, Olathe, KS (US)

(72) Inventors: Gary Wood, Olathe, KS (US); Jochen Harald Stritzker, La Jolla, CA (US)

(73) Assignee: TVAX BIOMEDICAL I, LLC, Olathe, KS (US)

( * ) Notice: Subject to any disclaimer, the term of this patent is extended or adjusted under 35 U.S.C. 154(b) by 146 days.

(21) Appl. No.: 16/939,266

(22) Filed: Jul. 27, 2020

(65) Prior Publication Data
US 2020/0353002 A1    Nov. 12, 2020

Related U.S. Application Data

(63) Continuation of application No. 15/757,687, filed as application No. PCT/US2016/050994 on Sep. 9, 2016, now abandoned.

(60) Provisional application No. 62/323,065, filed on Apr. 15, 2016, provisional application No. 62/255,294, filed on Nov. 13, 2015, provisional application No. 62/216,062, filed on Sep. 9, 2015, provisional application No. 62/216,046, filed on Sep. 9, 2015.

(51) Int. Cl.
| | |
|---|---|
| *A61K 35/17* | (2015.01) |
| *A61P 35/00* | (2006.01) |
| *A61K 35/768* | (2015.01) |
| *A61K 35/76* | (2015.01) |
| *A61K 39/00* | (2006.01) |

(52) U.S. Cl.
CPC ............ *A61K 35/768* (2013.01); *A61K 35/17* (2013.01); *A61K 35/76* (2013.01); *A61K 39/0011* (2013.01); *A61P 35/00* (2018.01); *A61K 2039/5158* (2013.01); *A61K 2039/545* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 6,406,699 B1 | 6/2002 | Wood | |
| 2002/0006409 A1 * | 1/2002 | Wood | A61P 35/00 424/93.7 |
| 2011/0064650 A1 * | 3/2011 | Szalay | A61P 35/00 424/9.1 |
| 2011/0319871 A1 | 12/2011 | Wood | |

FOREIGN PATENT DOCUMENTS

WO    WO 2014/170389 A1    10/2014

OTHER PUBLICATIONS

International Search Report and Written Opinion dated Feb. 6, 2017 for related PCT/US2016/50994, filed on Sep. 9, 2016 (26 pgs).
Melcher, et al., "Thunder and Lightning: Immunotherapy and Oncolytic Viruses Collide", Molecular Therapy (Published online Apr. 19, 2011) vol. 19, No. 6, pp. 1008-1016. (9 pgs).
Gujar SA, Lee PW. (2014) Oncolytic virus-mediated reversal of impaired tumor antigen presentation. Front Oncol. 4:77.
Nishio N, Diaconu I, Liu H, Cerullo V, Caruana I, Hoyos V, et al. (2014) Armed oncolytic virus enhances immune functions of chimeric antigen receptor-modified T cells in solid tumors. Cancer Res. 74:5195-205.
Yu F, Wang X, Guo ZS, Bartlett DL, Gottschalk SM, Song XT. (2014) T-cell engager-armed oncolytic vaccinia virus significantly enhances antitumor therapy. Mol Ther. 22:102-11.
Dudley, et al., "Adoptive-Cell-Transfer Therapy for the Treatment of Patients with Cancer", Nat Rev Cancer, vol. 3, No. 9, Sep. 2003, pp. 666-675 (20 pgs).
Rezvani, et al., "Cancer Vaccines and T Cell Therapy", Bio Blood Marrow Transplant, vol. 19, No. 1, Jan. 1, 2013, pp. S97-S101 (11 pgs).
Kottke, et al., "Broad Antigenic Coverage Induced by Vaccination with Virus-Based cDNA Libraries Cures Established Tumors", Nature Medicine, Nature Publishing Group, vol. 17, No. 7, Jul. 1, 2011, pp. 854-859 (7 pgs).
Pulido, et al., "Using Virally Expressed Melanoma cDNA Libraries to Identify Tumor-Associated Antigens that Cure Melanoma", Nature Biotechnology, vol. 30, No. 4, Apr. 2012, pp. 337-343 (8 pgs).
Bridle, et al., "Vesicular Stomatitis Virus as a Novel Cancer Vaccine Vector to Prime Antitumor Immunity Amenable to Rapid Boosting with Adenovirus", Molecular Therapy, Nature Publishing Group, GB, vol. 17, No. 10, pp. 1814-1821 (8 pgs).

* cited by examiner

*Primary Examiner* — Agnieszka Boesen
(74) *Attorney, Agent, or Firm* — Stinson LLP

(57) ABSTRACT

The present invention relates to augmenting the effects of adoptive T cell therapy, such as TVAX Immunotherapy, using adjunct treatment with an oncolytic virus, such as a vaccinia virus, to treat various types of cancer or other proliferative disorders. Immunomodulatory compounds can be used to further augment to effects of the therapy.

19 Claims, 1 Drawing Sheet

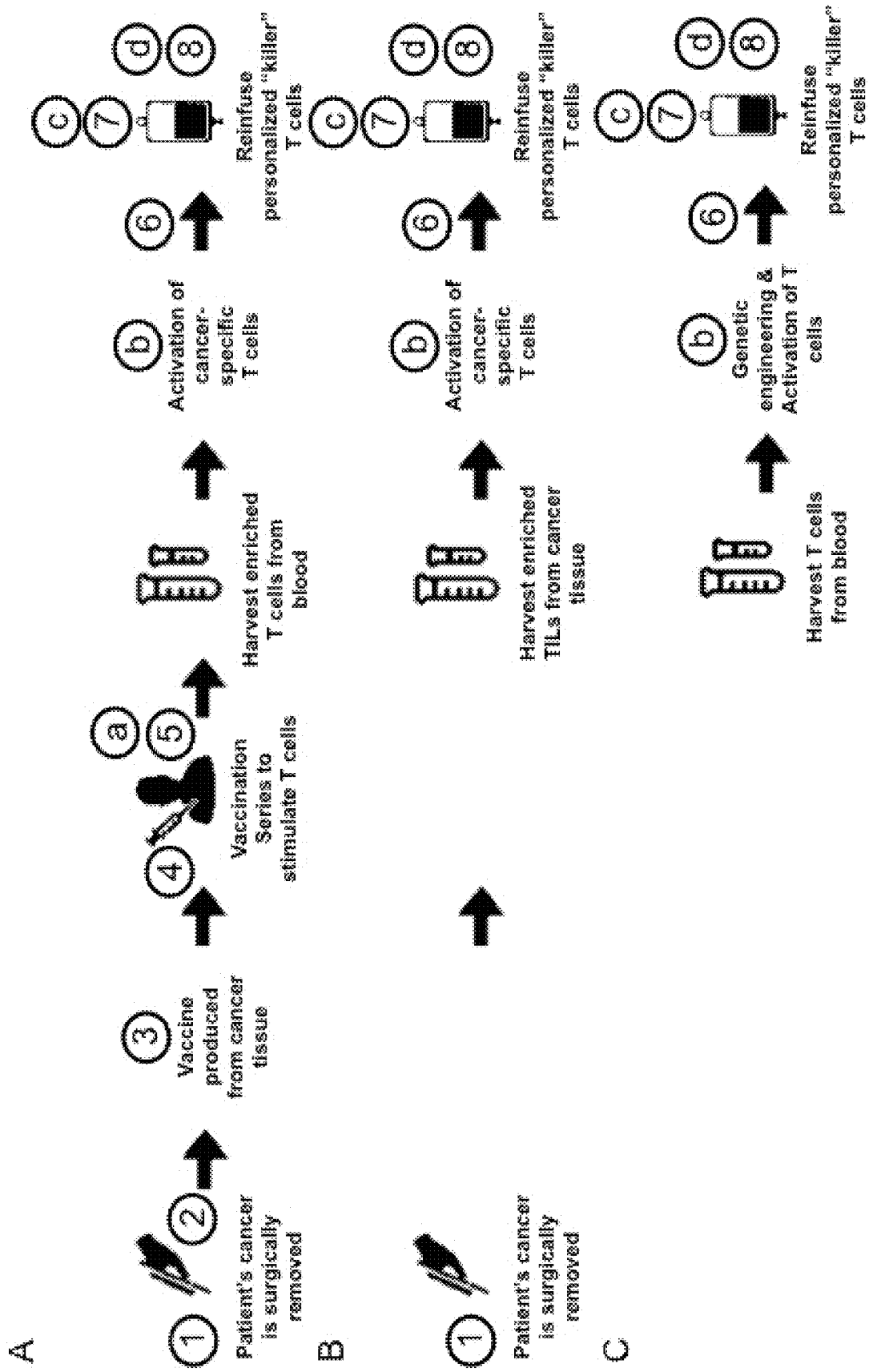

METHODS FOR COMBINING ADOPTIVE T CELL THERAPY WITH ONCOLYTIC VIRUS ADJUNCT THERAPY

CROSS-REFERENCE TO RELATED APPLICATIONS

This application claims priority to and is a Continuation of U.S. patent application Ser. No. 15/757,687, filed on Mar. 6, 2108, which is a 371 application from PCT/US2016/050994 filed on Sep. 9, 2016 which claims priority to the following U.S. Provisional Applications 62/216,046 filed on Sep. 9, 2015; 62/216,062 filed on Sep. 9, 2015; 62/255,294 filed on Nov. 13, 2015 and 62/323,065 filed on Apr. 15, 2016, each of which is incorporated herein by reference in its entirety.

BACKGROUND OF THE INVENTION

Cancer immunotherapy has gained renewed interest with the recent clinical successes achieved with immune modulating agents that are designed to overcome the cancer tissue-associated immune suppression. These agents enable the innate abilities of the human immune system to combat the cancer. Recent breakthroughs include cell-based therapies (e.g., ex vivo expanded, patient derived cancer neoantigen-specific T lymphocytes, T lymphocytes with genetically engineered T cell receptor (TCR), and chimeric antigen receptor (CAR)-T cell technology), oncolytic viruses (OV), monoclonal and genetically engineered antibodies (e.g., bi-specific T cell engager (BiTE) technology and immune checkpoint inhibitors (ICI)). These novel therapies are intended to fight cancer more effectively at both the primary cancer and at distant metastases, resulting in whole-body treatments with longer-term efficacy than current therapies, e.g. chemotherapy or radiation. Despite the promise of the individual treatment strategies in certain patient populations (e.g., hematologic malignancy and melanoma), these strategies have not been proven to produce significant clinical benefit in a high proportion of treated patients with diverse cancers.

BRIEF SUMMARY OF THE INVENTION

The present invention is directed to the field of cancer immunotherapy. Certain embodiments are directed to a cancer immunotherapy method for treating cancer in a patient comprising vaccinating the patient with a vaccine comprised of the patient's own malignancy and an immunologic adjuvant; isolating primed T lymphocytes from lymphoid tissue, peripheral blood or cancer tissue of the patient; stimulating the primed T lymphocytes to differentiate into effector T lymphocytes in vitro; stimulating the effector T lymphocytes to proliferate in vitro; administering an oncolytic virus to the patient; and infusing the effector T lymphocytes back into the patient.

In certain embodiments, the method further comprises administering a booster vaccination comprising a first oncolytic virus after the vaccination step and prior to the isolating primed T lymphocytes step and/or preceding the vaccinating step by administration of a first oncolytic virus within two weeks prior to the vaccinating step.

In certain aspects, the method may further comprise one or more of the following: after the infusing step, administering a second oncolytic virus to the patient; before the vaccinating step, administering a first oncolytic virus to the patient, and then removing the patient's own malignancy; before the vaccinating step, removing the patient's own malignancy and administering a first oncolytic virus to the patient, wherein administering the first oncolytic virus occurs simultaneously with or after the removing the patient's own malignancy; before the vaccinating step, removing the patient's own malignancy, combining the patient's own malignancy with a first oncolytic virus and using the combined virus/malignancy in the vaccinating step; and delivering a second oncolytic virus by the effector T lymphocytes in the infusion step.

In some embodiments, the present invention comprises a cancer immunotherapy method for treating cancer in a patient comprising isolating T lymphocytes from lymphoid tissue, peripheral blood or cancer tissue of the patient; optionally genetically engineering the T lymphocytes, which may include genetically engineering the T lymphocytes to express T cell receptors (TCR) or chimeric antigen receptors (CAR); stimulating the T lymphocytes to differentiate into effector lymphocytes in vitro; stimulating the effector T lymphocytes to proliferate in vitro; infusing the effector T lymphocytes back into the patient; and one or more of the following: administering an oncolytic virus to the patient after stimulating the effector T lymphocytes and prior to the infusing step; prior to the isolating step, administering the same or different oncolytic virus to the patient as a booster vaccine after vaccinating the patient with a vaccine comprised of the patient's own malignancy; prior to the isolating step, administering the same or different oncolytic virus to the patient prior to vaccinating the patient with a vaccine comprised of the patient's own malignancy; administering the same or different oncolytic virus to the patient after the infusing step; prior to the isolating step, administering the same or different oncolytic virus to the patient and then removing the patient's own malignancy prior to vaccinating the patient with the vaccine comprised of the patient's own malignancy; prior to the isolating step, removing the patient's own malignancy and then administering the same or different oncolytic virus to the patient prior to vaccinating the patient with the vaccine comprised of the patient's own malignancy; prior to the isolating step, removing the patient's own malignancy, combining the malignancy with the same or different oncolytic virus, and using the combined virus/malignancy to vaccinate the patient; and delivering the same or different oncolytic virus by the effector T lymphocytes in the infusion step.

In certain embodiments, the present invention comprises a cancer immunotherapy method for treating cancer in a patient comprising vaccinating the patient with a first oncolytic virus; isolating primed T lymphocytes from the peripheral blood, lymphoid tissue or cancer tissue of the patient; stimulating the primed T lymphocytes to differentiate into effector lymphocytes in vitro; stimulating the effector T lymphocytes to proliferate in vitro; and infusing the effector T lymphocytes back into the patient. In certain aspects, the cancer is inoperable. The method may further comprise one or more of: administering a second oncolytic virus to the patient after stimulating the T lymphocytes and prior to the infusing step; administering the same or different second oncolytic virus to the patient as a booster vaccine after the vaccinating step; administering a the patient's own malignancy and an immunologic adjuvant to the patient as a booster vaccine after the vaccinating step; administering the same or different second oncolytic virus to the patient after the infusing step; prior to the vaccinating step, administering the same or different second oncolytic virus to the patient and then removing the patient's own malignancy; prior to the vaccinating step, removing the patient's own malignancy and then administering the same or different second oncolytic virus to patient; prior to the vaccinating step, removing the patient's own malignancy, combining the malignancy with the same or different second oncolytic virus, and using the combined virus/malignancy as an additional vaccinating step; and delivering the same or different oncolytic virus by the effector T lymphocytes in the infusion step.

In some aspects of the invention, including each of the embodiments described above, the oncolytic virus may be selected from the group consisting of vaccinia virus, reovirus, measles virus, mumps virus, adenovirus and herpes virus, vesicular stomatitis virus, newcastle disease virus, parvovirus, poliovirus, coxsackie virus, sindbis virus, seneca valley virus, maraba virus and combinations thereof. The oncolytic vaccinia virus may selected form the group consisting of Lister, Western Reserve (WR), Copenhagen (Cop), Bern, Paris, Tashkent, Tian Tan, Wyeth (DRYVX), IHD-J, IHD-W, Brighton, Ankara, CVA382, Modified Vaccinia Ankara (MVA), Dairen I, LC16m8, LC16M0, LIVP, ACAM2000, WR 65-16, Connaught, New York City Board of Health (NYCBH), EM-63 and NYVAC strain, and combinations thereof. In certain aspects of the invention, the oncolytic vaccinia virus may be selected from the group consisting JX594 and derivatives thereof, WO-12 and derivatives thereof, the GL-ONC1 (i.e., GLV-1h68) and derivatives thereof, clonal strains of LIVP and Copenhagen, and combinations thereof.

In some aspects of the invention, including each of the embodiments described above, the cancer to be treated may consist of bladder cancer, breast cancer, prostate cancer, basal cell carcinoma, biliary tract cancer, bladder cancer, bone cancer, brain and central nervous system cancer (e.g., glioma), adenocarcinomas, lung cancer, cervical cancer, choriocarcinoma, colon and rectum cancer, connective tissue cancer, cancer of the digestive system; cancer of the small intestine and cecum; endometrial cancer, esophageal cancer; eye cancer; cancer of the head and neck; gastric cancer; intra-epithelial neoplasm; kidney cancer; larynx cancer; leukemia; liver cancer; gall bladder cancer lung cancer (e.g., small cell and non-small cell); lymphoma including Hodgkin's and Non-Hodgkin's lymphoma; melanoma; myeloma, neuroblastoma, oral cavity cancer (e.g., lip, tongue, mouth, and pharynx); cancer of the salivary glands; ovarian cancer; pancreatic cancer, retinoblastoma; rhabdomyosarcoma; rectal cancer, renal cancer, cancer of the respiratory system; sarcoma, skin cancer; stomach cancer, testicular cancer, thyroid cancer; uterine cancer, cancer of the urinary system, as well as other carcinomas and sarcomas. In certain aspects, the cancer is selected from the group consisting of breast cancer, brain and central nervous system cancer, kidney cancer, and ovarian cancer.

In some aspects of the invention, including each of the embodiments described above, the oncolytic virus may be genetically engineered to include deletion of a gene encoded by the wild-type strain of the virus, wherein the genes encodes immune modifying gene product(s), metabolic gene product(s), or cell cycle controlling gene product(s), and/or the oncolytic virus may be genetically engineered to encode a gene product selected from the group consisting of an anti-cancer agent, an anti-angiogenic agent, an immunomodulatory molecule or an antigen (e.g., cancer (neo)antigens, cancer-associated antigens, tissue-specific antigens, bacterial antigens, viral antigens, yeast antigens, fungal antigens, protozoan antigens, parasite antigens and mitogens), a hormone, a growth factor, a cytokine, a chemokine, a costimulatory molecule, a ribozyme, a transporter protein, a single chain antibody (e.g., an anti-VEGF or anti-VEGFR, or anti-EGFR antibody), an antibody (agonistic or antagonistic) against immune modulating proteins, an antisense or ds RNA or other RNA product, a prodrug converting enzyme, an siRNA, a microRNA, a toxin, an anti-cancer oligopeptide, a mitosis inhibitor protein, an antimitotic oligopeptide, an anti-cancer polypeptide antibiotic, an angiogenesis inhibitor, a cancer suppressor, a cytotoxic protein, a cytostatic protein, an enzyme that modifies a substrate to produce a detectable product or signal, an enzyme detectable by antibodies, a protein that can bind a contrasting agent.

In some aspects of the invention, including each of the embodiments described above, the method may further comprise administering one or more, for example 2 to 6, immunomodulatory compounds. In certain aspects, the immunomodulatory compound may be infused into the patient with the effector T lymphocytes, administered to the patient after the infusing step, administered to the patient after the vaccinating step and prior to the isolating of primed T lymphocytes step, and/or delivered to the primed T lymphocytes between the isolating step and the infusing step. The immunomodulatory compound is delivered to the primed T lymphocytes during the differentiation step, the proliferation step, or both. In certain aspects, the immunomodulatory compound is selected from the group consisting of compounds that bind to or otherwise interfere with the function of immune-inhibitory signaling molecules, agonistic compounds that activate or augment the immunostimulatory signaling molecules, and combinations thereof. The immunostimulatory signaling molecule may be selected from the group consisting of TNF and TNFR superfamily molecules, B7 and CD28-related proteins, NK cell targets, soluble mediators, immune checkpoint ligands and receptors, toll-like receptor family molecules, phopshatidylserine, SIRPA-CD47, VEGF, neuropilin and combinations thereof. In certain aspects, the immunomodulatory compound is selected from the group consisting of Ipilimumab, Pembrolizumab, Nivolumab, Atezolizumab, and combinations thereof. In certain aspects, the immunomodulatory compound is selected from the group consisting of genetically engineered antibodies, natural ligands, small molecules, and combinations thereof.

BRIEF DESCRIPTION OF THE DRAWINGS

FIG. 1 depicts various adoptive T cell therapy schemes of the present invention comprising steps for using oncolytic virus (1-8) and steps for using immunomodulatory compounds (a-d) with TVAX Immunotherapy (A), TIL immunotherapy (B), and TCR/CAR-T immunotherapy (C).

DETAILED DESCRIPTION OF PREFERRED EMBODIMENT

Unless defined otherwise, all technical and scientific terms used herein have the same meaning as is commonly understood by one skilled in the art to which the invention(s) belong. The terms "a" or "an" may mean one or more. As used herein in the claim(s), when used in conjunction with the word "comprising," the words "a" or "an" may mean one or more than one.

The present invention relates to augmenting the effects of adoptive T cell therapy using adjunct treatment with an oncolytic virus, such as a vaccinia virus, to treat various types of cancer or other proliferative disorders. Although the present invention contemplates use of an oncolytic virus with various types of adoptive T cell therapy, it is particularly useful in connection with what is referred to herein as the "TVAX Immunotherapy," which is described in detail in Section 8, below, and in U.S. Pat. No. 6,406,699, which is incorporated herein by reference in its entirety.

An exemplary embodiment of the TVAX immunotherapy is shown as administration route A in FIG. 1 and comprises the steps of:

vaccinating a patient with a vaccine comprised of a patient's own malignancy and an immunologic adjuvant, isolating primed T lymphocytes from the lymphoid tissue, peripheral blood or cancer tissue of the patient, stimulating the primed T lymphocytes to differentiate into effector T lymphocytes in vitro, stimulating effector T lymphocytes to proliferate in vitro, and infusing the effector T lymphocytes back into the patient.

The TVAX Immunotherapy may also comprise the step of removing the patient's own malignancy and using the patient's own malignancy to create the vaccine comprising the patient's own malignancy. It should be understood that when used in this application, "removal" of cancer cells means removing at least a portion of the cancer cells, unless otherwise specified.

As described in more detail below, the oncolytic virus can be administered at any step of the TVAX Immunotherapy process, as exemplified in FIG. 1 by the numbers 1-8 in connection with administration route A. Further, the oncolytic virus can be administered at only one step of the TVAX Immunotherapy process or at multiple steps of the process. When an oncolytic virus is administered at more than one step in the process, either the same or different oncolytic viruses can be used in each of the multiple administration.

Exemplary oncolytic viruses useful in combination with the TVAX Immunotherapy are described in Section 5, below, and include vaccina viruses and the virus technology described in PCT Application WO 2015/103438 and WO 2012/142529, both of which are incorporated by reference in their entireties. The oncolytic viruses may be administered in multi-dose and single dosage amounts. Exemplary dosages for viruses that form plaques, include, but are not limited to between or about between $1\times10^5$ and $1\times10^{12}$ pfu, $1\times10^6$ to $1\times10^{10}$ pfu, $1\times10^7$ to $1\times10^{10}$ pfu, each inclusive, such as at least or about at least or $1\times10^6$, $1\times10^7$, $1\times10^8$, $1\times10^9$, $2\times10^9$, $3\times10^9$, $4\times10^9$, $5\times10^9$ pfu, $1\times10^{10}$ pfu, $2\times10^{10}$ pfu, $3\times10^{10}$ pfu, $4\times10^{10}$ pfu.

The methods described herein can also be used with other adoptive T cell therapies, including tumor-infiltrating lymphocyte (TIL) technology, as shown in administration route B in FIG. 1, and genetically engineered T lymphocytes (e.g., TCR, CAR T), as shown in administration route C in FIG. 1. TIL and TCR/CAR T therapies are described in more detail in Section 8, below.

The methods of the present invention may also comprise the use of an immunomodulatory compound, as shown by the letters a-d in FIG. 1. Exemplary immunomodulatory compounds useful in combination with the TVAX Immunotherapy and other adoptive T cell therapies are described in Section 6, below.

It should be understood that one or more of the oncolytic virus and/or immunomodulatory compound administration steps can be used in combination. It should also be understood that FIG. 1 shows exemplary embodiments of the methods of the present invention, and is not intended to limit the invention. Although certain embodiments will be described in reference to FIG. 1, it should be understood the invention should not be limited to any one embodiment and should only be limited by the claims. For clarity of disclosure, and not by way of limitation, the detailed description is divided into the subsections that follow.

1. USE OF ONCOLYTIC VIRUS TO PREPARE CANCER TISSUE FOR ADOPTIVE T CELL IMMUNOTHERAPY

In one preferred embodiment, as shown at Step 6 in administration routes A, B and C in FIG. 1, the oncolytic virus is administered to the patient shortly before the primed T lymphocytes, which were activated ex vivo into cancer neoantigen-specific effector T lymphocytes, are infused back into the patient. Suitable oncolytic viruses include the vaccina virus and the other viruses discussed in Section 5, below. The injected oncolytic virus colonizes the cancer tissue left behind following surgical removal of the primary cancer and/or metastases. This leads to a local inflammatory response and to conversion of the cancer microenvironment from being immunosuppressive to being immunostimulatory. This strongly favors the anti-cancer activities of the infused cancer neoantigen-specific effector T lymphocytes that were activated ex vivo but need to maintain and/or increase their activity following their entry into cancer tissue. This is different from preconditioning with immunomodulatory compounds that are intended to simply kill the suppressor effect of the cancer environment. The detailed mechanism of action is described in more detail later in this section.

The use of an oncolytic virus in combination with the TVAX Immunotherapy provides the opportunity to create unique synergies. Because the TVAX Immunotherapy utilizes a vaccination prior to isolating the primed T lymphocytes, there is an increased number of T lymphocytes in the remaining cancer tissue that are available to receive the benefits provided by the oncolytic virus. This creates an environment that can produce a markedly increased number of differentiated effector T lymphocytes in situ.

Further, when a highly immunogenic oncolytic virus with low toxicity, such as the vaccinia virus described herein, is used, the oncolytic virus can be administered intravenously, which allows it to reach and colonize all cancer tissues. This is a benefit over the use of highly toxic oncolytic viruses that requires injection of the virus only into tissue that can be reached for viral injection.

Although intravenous administration is a preferred route of administration for the oncolytic virus, the oncolytic virus may also be administered by other systemic routes (e.g. intra-arterial injection), or may be administered regionally (e.g., intraperitoneal, intrapleureal injection), and/or directly into the malignancy either as infusion or direct injection (e.g., intra-tumoral, intra-metastatic injection) or combinations of the above.

The oncolytic virus may be administered to the patient within two weeks prior to, within 7 days prior to, or up to the day of, infusing the effector T lymphocytes back into the patient. In one embodiment the oncolytic virus is administered simultaneously with the infusion of the effector T lymphocytes back into the patient. If administering an oncolytic virus prior to infusion is combined with one or more other steps involving use of an oncolytic virus, the same or different oncolytic virus may be used in each step.

The mechanism of action of administering the oncolytic virus prior to infusion of the effector T lymphocytes in the present invention is explained in more detail in the following paragraphs:

General

Exposure of a naïve host to a foreign agent such as a virus results in a cascade of events that involve local inflammation at the disease site and the development of a systemic immune response that ultimately leads to the release of antigen-primed T lymphocytes and antibodies from lymphoid tissue into the blood. Unless the foreign agent has developed protective mechanisms that allow it to avoid the immune response that develops, antigen-primed T lymphocytes enter diseased tissue and differentiate into effector T lymphocytes to eliminate the agent. When the agent is one of the agents that are eliminated by T lymphocytes, i.e., obligate intracellular parasites, the T lymphocytes enter the inflamed disease tissue, encounter activated antigen-presenting cells expressing antigens from the foreign agent and are activated to differentiate into antigen-specific effector T lymphocytes. Those activated antigen-specific effector T lymphocytes then initiate a cascade of local events that results in the elimination of the foreign agent, generally by killing cells that are infected with the foreign agent.

Cancer (cancer cells are genetically foreign to the host) is a foreign agent that stimulates a chronic inflammatory response that, rather than helping to eliminate the cancer, promotes its development and suppresses the differentiation of antigen-primed T lymphocytes into effector T lymphocytes. Generally, unless the cancer tissue is perturbed in some way, cancer fails to stimulate the development of an immune response and the cancer progresses in apparent obliviousness to the fact that cancer cells are foreign agents and have the potential to be killed and eliminated by cancer neoantigen-specific effector T lymphocytes. Cancer tissue contains cells, e.g. myeloid derived suppressor cells (MDSCs) and cancer-associated macrophages, which prevent the formation of effector T lymphocytes and suppress the stimulation of an immune response. Macrophages in principle have the capacity to be stimulated to become antigen presenting cells and present cancer antigen, but, during the natural progression of a cancer, they do not develop that capacity. Macrophages are highly plastic cells that have the ability to be stimulated to express a variety of functions. Cancer-associated macrophages promote cancer tissue growth and spread, not antigen presentation and killing of cells harboring a foreign agent or normal cells expressing foreign antigens, e.g., cancer cells (another of their plastic functions). It is for these and other reasons that cancer progresses to kill its host.

It is possible to vaccinate a cancer patient with their own cancer cells and induce an immune response against the foreignness expressed by the cancer cells, which leads to production of large numbers of primed cancer neoantigen-specific T lymphocytes that leave lymphoid tissue and travel through blood to enter cancer tissue. However, that does not change the nature of the MDSCs and macrophages resident in cancer tissue, as evidenced by the failure of cancer vaccines to exhibit significant therapeutic effects. That is why cancer vaccines usually produce minimal therapeutic benefit, at best, despite the fact that exposure of the immune system to the foreignness of cancer cells results in the development of a strong systemic immune response.

The fact that cancer tissue-associated T lymphocytes fail to develop into effector T lymphocytes that produce significant therapeutic benefit can be rectified by: A) isolating the primed cancer neoantigen-specific T lymphocytes from cancer tissue, lymphoid tissue or preferably blood of cancer patients (cancer patients vaccinated with their own malignancy in the context of the TVAX immunotherapy), B) stimulating those primed T lymphocytes to develop into cancer neoantigen-specific effector T lymphocytes ex vivo and C) using adoptive cell transfer (ACT) to deliver those ex vivo-activated cancer neoantigen-specific effector T lymphocytes into the patient's blood where they can travel through the blood, enter cancer tissue and initiate a cascade of effects that leads to efficient cancer cell killing and rejection of the cancer. This approach can produce durable clinical effects in a significant number of treated patients. However, not all patients that are treated by adoptive cell transfer with cancer neoantigen-specific effector T lymphocytes respond to the therapy and not all patients that respond are cured.

Certain Embodiments of Preparing Cancer Tissue with an Oncolytic Virus

The present invention incorporates oncolytic virus delivery to produce significant pro-inflammatory and immunostimulatory changes in the cancer microenvironment, which enables adoptively transferred cancer neoantigen-specific effector T lymphocytes to act more efficiently. Oncolytic viruses delivered systemically, regionally and or directly, enter cancer tissue and enter cancer cells and cause lysis, which results in the release of pathogen-associated molecular patterns (PAMPs) and danger-associated molecular patterns (DAMPs). These changes result in the activation of the innate immune system and are likely to change the cancer microenvironment by converting local antigen presenting cell precursors into antigen presenting cells and by causing professional antigen presenting cells (e.g., monocytes, macrophages, dendritic cells) to infiltrate the cancer tissue, i.e., recruiting additional antigen presenting cells. In addition, the oncolytic virus may also enter cancer tissue-associated macrophages and stimulate their development into antigen presenting cells. The resulting changes in the cancer microenvironment prevent the infused cancer neoantigen-specific effector T lymphocytes from having their effector functions depressed by resident suppressor cells/factors following their arrival in cancer tissue so that more of the T lymphocytes are produced locally and these T lymphocytes are able to more effectively kill cancer neoantigen expressing cells, i.e., cancer cells.

Thus, the exposure of the patient (a cancer cell-vaccinated patient in the context of the TVAX Immunotherapy) to an oncolytic virus immediately prior to adoptive cell transfer with cancer neoantigen-specific effector T lymphocytes prepares cancer tissue throughout the body to receive those cancer neoantigen-specific effector T lymphocytes in a way that maximizes their therapeutic effects.

In the process of the present invention, immune cells are collected, for example from the blood, and stimulated ex vivo to develop into cancer neoantigen specific effector T lymphocytes. While they are being stimulated, the patient is exposed to an oncolytic virus in a dose and form that produces maximal suppression of immunosuppressive effects and activation of immune enhancing effects within the cancer microenvironment. Minimal side effects result from this procedure, while significant improvements of the adoptive T lymphocyte therapy effects occur. In the TVAX Immunotherapy, patients are first vaccinated, further improving the ability of the cancer tissue to produce large numbers of effector T lymphocytes after infusion with the cancer neoantigen specific effector T lymphocytes.

2. USE OF ONCOLYTIC VIRUS AS VACCINE IN TVAX IMMUNOTHERAPY

In certain embodiments of the present invention utilizing the TVAX Immunotherapy, the oncolytic virus is injected as a vaccination in place of vaccinating with the patient's own malignancy. Suitable oncolytic viruses include the vaccina virus and the other viruses discussed in Section 5, below. Vaccination with the oncolytic virus can be the sole vaccination method, either as a single vaccination using the oncolytic virus, or an initial vaccination followed by one or more oncolytic virus booster vaccinations, as represented by Step 4 alone, or in combination with Step 5 in administration route A of FIG. 1. The oncolytic virus could be administered systemically, regionally, and/or directly into the malignancy either as an infusion or direct injection, or combinations of the above. In one embodiment, the oncolytic virus could be administered both as a primary vaccination intra-tumorally, and as a booster vaccination (s) through some other route. The timing of the various injections can vary over a relatively wide range depending on the type of cancer but generally would be separated by a period of 1-2 weeks. The vaccination and booster could use the same, or different, oncolytic virus.

This method of vaccination could be performed, for example, when surgical removal of cancer tissue is not medically feasible, i.e., the cancer is inoperable, such that a vaccine comprised of the patient's own malignancy cannot be produced. It can also be used when not enough cancer cell materials can be obtained to produce a vaccine. Using the oncolytic virus as the vaccination in the TVAX Immunotherapy also means that less, or no, adjuvant (e.g. GM-CSF) would be needed. The oncolytic virus also provides potential benefits resulting from the oncolytic virus vaccination stimulating an immune response throughout the body by taking the antigen to the immune system from the cancer wherever it is.

More specifically, in the combination of oncolytic virus with adoptive cell therapy, the oncolytic virus may: 1) enter cancer tissue throughout the body from the blood following intravenous administration, 2) start lytic replication cycles, 3) generate an inflammatory response within the cancer and 4) produce a systemic immune response against the cancer's neoantigens.

As noted above, there are at least two benefits of this virus-dependent vaccination approach: A) it is useable against any cancer, whether operable or inoperable, and B) it stimulates immune responses in lymphoid tissue throughout the body, thus maximizing the number of primed cancer neoantigen-specific T lymphocytes present in the body. Moreover, the oncolytic virus can be genetically engineered to produce cancer (neo)antigens and/or immunostimulatory factors, such as GM-CSF and Fms-related tyrosine kinase 3 (FLT3) ligand, both of which are immunological adjuvants on their own and are anticipated to augment the immune response-generating effects of the oncolytic virus itself. It is possible that the therapeutic effects of vaccination are limited because the cancer suppresses the late stages of the cascade of events that lead to generation of effector T lymphocytes that are capable of efficient cancer cell killing and rejection of the cancer. This cascade of events occurs when primed cancer neoantigen-specific T lymphocytes that have left lymphoid tissue and traveled through blood to enter cancer tissue and, following entry into cancer tissue, differentiate into cancer neoantigen-specific effector T lymphocytes.

The outcome of the therapy is improved by: A) allowing time for an immune response to develop, B) isolating primed cancer neoantigen-specific T lymphocytes from the patient, C) stimulating primed cancer neoantigen-specific T lymphocytes to develop into cancer neoantigen-specific effector T lymphocytes ex vivo and then D) delivering those ex vivo-activated cancer neoantigen-specific effector T lymphocytes into the patient's blood where they can travel through the blood, enter cancer tissue and initiate a cascade of effects that leads to efficient cancer cell killing and rejection of the cancer.

In addition to being used as the sole vaccination in the TVAX Immunotherapy system, the oncolytic virus vaccination can also be used in combination with vaccinating with the patient's own malignancy. Suitable oncolytic viruses include the vaccina virus and the other viruses discussed in Section 5, below. The oncolytic virus can be used either as a booster after the initial vaccination with the patient's own malignancy, as in Step 5 of administration route A in FIG. 1, and/or as an initial vaccination followed with a booster vaccination with the patient's own malignancy, as in Step 4 of administration route A in FIG. 1. In each case in this embodiment, the oncolytic virus vaccination occurs after removal of the malignancy, which is used to make the vaccine comprising the patients' own malignancy. This combination vaccination approach also has the benefit of requiring fewer cancer cells and adjuvants than the traditional TVAX Immunotherapy and would allow the oncolytic virus to stimulate the immune response throughout the body.

When used as a vaccine in combination with a separate vaccination with the patient's own malignancy, the oncolytic virus could be administered systemically, regionally, and/or directly into the malignancy either as infusion or direction injection, or combinations of the above. The timing of the various injections can vary over a relatively wide range depending on the type of cancer but generally would be separated by a period of 1-2 weeks.

More specifically, this second iteration of this general strategy is possible in cases where: A) surgery is performed for therapeutic benefit and/or B) is possible and is performed to produce a condition of minimal disease. In this situation, if the surgery produced a sufficient number of cancer cells to produce an autologous cancer vaccine, the systemic, local or direct oncolytic virus-based vaccination approach outlined above is combined with intradermal vaccination with attenuated autologous cancer cells. The attenuated autologous cancer cell vaccines are injected in a series of one or more vaccinations, which occur either before the virus is injected, and/or at the same time that the patient is receiving the genetically engineered oncolytic virus, and/or as a subsequent booster vaccination. The timing of the various injections can vary over a relatively wide range depending on the type of cancer but generally would be separated by a period of 1-2 weeks. The benefit of this combination is that generally the immune system is organized to respond optimally to foreign threats that come in through external surfaces, not those that arise as threats from within, i.e., a progressing cancer. Often, the cancer is growing in tissues that do not have efficient lymphoid drainage but, even when cancers are growing in sites with extensive lymphoid drainage, i.e., external body surfaces, the cancer is not viewed by the body as a foreign threat. Thus, the coincident combination of the two vaccination strategies should have synergistic effects with regard to generating efficient immune response against the patient's cancer.

If administering an oncolytic virus prior as a vaccination step is combined with one or more other steps involving use of an oncolytic virus, the same or different oncolytic virus may be used in each step.

3. OTHER USES OF ONCOLYTIC VACCINES IN ADOPTIVE T CELL THERAPY

Injection of Oncolytic Virus Before Surgical Removal of the Primary Cancer in TVAX Immunotherapy As represented by Step 1 in administration route A in FIG. 1, injection of oncolytic virus before surgical removal of the patient's own malignancy can augment the vaccination steps in the TVAX Immunotherapy protocol. Cancer infection results in reduction of the immunosuppressive properties of the cancer microenvironment and leads to immunostimulation. The result is that a higher percentage of cancer neoantigen-specific T lymphocytes can be obtained from a patient. The overall yield (and quality) of re-infused effector T lymphocytes are enhanced. The oncolytic virus could be administered systemically, regionally, and/or directly into the malignancy either as infusion or direct injection. The oncolytic virus may be administered to the patient within two weeks prior to, within 7 days prior to, or up to the day of, the surgical removal, preferably within 7 days prior to removal. Suitable oncolytic viruses include the vaccina virus and the other viruses discussed in Section 5, below. If administering an oncolytic virus in this embodiment is combined with one or more other steps involving use of an oncolytic virus, the same or different oncolytic virus may be used in each step.

Application of Oncolytic Virus Following Cancer Removal in TVAX Immunotherapy

As represented by Step 2 in administration route A in FIG. 1, an oncolytic virus may be administered into the cancer bed following removal of the patient's own malignancy (e.g. debulking surgery) in the TVAX Immunotherapy to improve the elimination of minimal residual disease and stimulate the generation of an anti-cancer immune response as discussed above. Application of an oncolytic virus at the same time, immediately after, or shortly after, such removal results in better control of metastases (depending on cancer stage) because of the anti-cancer effects of the oncolytic virus. The oncolytic virus could be administered systemically, regionally, and/or directly into the malignancy either as infusion or direct injection, preferably intravenously. Preferably, the oncolytic virus is administered into the cancer bed directly as infusion or direct injection. The oncolytic virus may be administered to the patient within one month after, within two weeks after, within 7 days after, or on the day of, the surgical removal, preferably within two weeks after removal. Suitable oncolytic viruses include the vaccina virus and the other viruses discussed in Section 5, below. If administering an oncolytic virus in this embodiment is combined with one or more other steps involving use of an oncolytic virus, the same or different oncolytic virus may be used in each step.

Combination of Vaccine Comprising the Patient's Own Malignancy with Oncolytic Virus in TVAX Immunotherapy As represented by Step 3 in administration route A in FIG. 1, an additional opportunity exists in the ex vivo combination of cancer cells in the TVAX Immunotherapy with an oncolytic virus, e.g., vaccinia virus, and using the combined virus/cancer cells for intradermal vaccination. This will result in an improved cancer vaccine and allow for decreased use of other immunological adjuvants (e.g., granulocyte macrophage colony-stimulating factor [GM-CSF]). In such a process, the cancer cells may simply be mixed with the virus being re-injected as a vaccine. Alternatively, the cancer cells may be infected with the oncolytic virus ex vivo before being re-injected into the patient as a vaccine. The cancer cells may be infected by mixing the oncolytic virus and cancer cells and incubating for a period of time, e.g. 60 minutes, in cell culture medium. When used here, the term combined virus/cancer cells will encompass both mixed and infected cancer cells.

More specifically, the combined virus/cancer cells will result in production of "danger signals" that lead to adjuvantizing effects thereby enhancing the efficacy of the immunization through additional stimulation of antigen presenting cells. Again, genetic modification of the oncolytic virus by introduction of genes encoding for cancer antigens, immunomodulatory genes and/or deletion of immune inhibitory genes are additional ways to enhance viral stimulation.

Suitable oncolytic viruses include the vaccina virus and the other viruses discussed in Section 5, below. If administering an oncolytic virus in this embodiment is combined with one or more other steps involving use of an oncolytic virus, the same or different oncolytic virus may be used in each step.

Re-Stimulation of Cancer Tissue-Associated T Lymphocytes after Adoptive Cell Transfer As represented by Step 8 in administration routes A, B and C in FIG. 1, an oncolytic virus may be administered after the patient is infused with the ex vivo-activated effector T lymphocytes by adoptive cell transfer in the TVAX Immunotherapy or other adoptive cell transfer therapy. This administration of the oncolytic virus could result in re-stimulation of cancer tissue-associated T lymphocytes that may have become inactive over time. The oncolytic virus may be administered within 60 days, 30 days, two weeks or 7 days after the patient is infused with the effector T lymphocytes. The oncolytic virus could be administered systemically, regionally, and/or directly into the malignancy either as infusion or direct injection, preferably intravenously.

Suitable oncolytic viruses include the vaccina virus and the other viruses discussed in Section 5, below. If administering an oncolytic virus in this embodiment is combined with one or more other steps involving use of an oncolytic virus, the same or different oncolytic virus may be used in each step.

Delivery of Oncolytic Virus Via Engineered Cancer-Targeting Cells

As represented by Step 7 in administration routes A, B and C of FIG. 1, the oncolytic virus may be delivered via engineered cancer-targeting cells, such as the infused T lymphocytes in the TVAX Immunotherapy or other adoptive cell transfer therapy. The cells act as a ferry for the oncolytic virus, but also protect their viral load from being attacked by antibodies and/or complement in the patient's blood. Consequently, higher amounts of oncolytic virus would be delivered to the cancer and its metastases, thereby enhancing the T lymphocytes' therapeutic effects. The oncolytic virus and the effector T lymphocytes would be mixed together in vitro prior to infusion. The virus attaches to the T lymphocytes and/or infects the T lymphocytes and the T lymphocytes carry the virus into the cancer following infusion.

Suitable oncolytic viruses include the vaccina virus and the other viruses discussed in Section 5, below. If administering an oncolytic virus in this embodiment is combined with one or more other steps involving use of an oncolytic virus, the same or different oncolytic virus may be used in each step.

Other Potential Uses of Oncolytic Viruses in Adoptive T Cell Therapy

Additional further embodiments for use in the TVAX Immunotherapy or other adoptive cell transfer therapy include delivery of payloads by the oncolytic virus (e.g., cytokines encoded in the genome of the oncolytic virus, or additional expression of cancer associated (neo)antigens). This could augment the effects of oncolytic virus at any of the various proposed usage steps and/or steer the immune response in a particular direction that would have the result of preferential production of T lymphocyte subsets that have the capacity to generate greater therapeutic benefits, e.g. toward a cytotoxic T lymphocyte predominant immune response.

Alternative adoptive cell transfer preparative and/or pre-conditioning treatments (such as lymphodepletion and/or irradiation) as well as co-treatment with immunomodulatory compound(s) are other treatment combinations that can be incorporated into a treatment schedule that involves injection of an oncolytic virus, e.g., oncolytic vaccinia virus.

4. IMMUNOMODULATORY COMPOUND(S) TO AUGMENT ADOPTIVE T CELL IMMUNOTHERAPEUTIC EFFECTS

Immunomodulatory compounds can be used at various steps in the process of the present invention to augment the T cell immunotherapy effects in the TVAX Immunotherapy or other adoptive cell transfer therapy. Immunomodulatory compounds may be used at one step or multiple steps and may be used in combination with one or more administrations of an oncolytic virus. The immunomodulatory compound may be administered systemically, regionally and/or directly into the malignancy either by infusion or by direct injection, preferably intravenously. When more immunomodulatory compounds are used at multiple steps, the immunomodulatory compounds used at each step may be the same or different and the administration route at each step may be the same or different.

The immunomodulatory compound(s) may be administered in multi-dose and single dosage amounts, including, but not limited to between or about between 1 pg and 1 kg, 1 µg to 1 g, 1 mg to 1 g, each inclusive, such as at least or about at least or 1 pg, 10 pg, 100 pg, 1 ng, 10 ng, 100 ng, 1 µg, 10 µg, 100 µg, 1 mg, 10 mg, 100 mg, 1 g, 10 g, 100 g, 1 kg.

General

There are two major classes of immunomodulatory compounds: Compounds that interfere with the function of immunoinhibitory signaling molecules (e.g., ICI) and compounds that activate/augment the immunostimulatory signaling molecules (e.g., co-stimulatory molecule agonists). In the context of vaccination and adoptive T cell immunotherapy, those immunomodulatory compounds can play critical roles that lead to augmented therapeutic effects.

Vaccination with autologous cancer stimulates an immune response that primes T lymphocytes against cancer neoantigens. Exposure to a specific antigen can, for example, result in upregulation of co-stimulatory molecules (e.g., 4-1BB, OX40, GITR, TNFRSF25, and ICOS). However, several mechanisms in the patient's body prevent primed T lymphocytes from becoming fully activated effector T lymphocytes, which would result in complete eradication of the cancer. Among those inhibitory mechanisms, the stimulation of immunoinhibitory signaling molecules that are expressed on T lymphocytes (e.g., CTLA-4, PD-1, LAG3, and TIM3) can result in inhibition of T lymphocyte activation.

Providing immunomodulatory compound(s) to the patient can counteract some of those mechanisms. These immunomodulatory compound(s) can lead to the generation of a higher concentration and/or more potent cancer neoantigen-specific T lymphocytes, which can then be isolated from the patient and serve as basis for an enhanced ex vivo T lymphocyte activation/expansion process.

The ex vivo activation and/or expansion process that is necessary for production of adoptive T cell immunotherapy products can also benefit from immunomodulatory compound(s). In a preferred embodiment, the use of agonistic compounds will activate co-stimulatory molecules on T lymphocytes (e.g., 4-1BB, OX40, GITR, TNFRSF25, and ICOS). This results in enhanced expansion and anticancer function and can lead to augmented T lymphocyte survival and persistence in the cancer patient.

Administration of immunomodulatory compound(s) to patients during and/or after adoptive T cell immunotherapy will enhance their therapeutic effects. Disruption of immunoinhibitory signals will prevent T lymphocyte inactivation and result in persistent anti-cancer activity. Similarly, additional activation of immunostimulatory molecules will enhance their effector functions against cancer cells. Repeated administration of immunomodulatory compound(s) could lead to longer lasting therapeutic effects.

Immunomodulatory Compound(s) as Boosting Agents for T Lymphocyte Response Development after Vaccination As represented by Step (a) in administration route A in FIG. 1, administration of non-viral immunomodulatory compound(s) to patients who were vaccinated with their own cancer cells in the TVAX Immunotherapy could result in an augmented T lymphocyte response against cancer neoantigen-specific antigens. Depending on the type of immunomodulatory compound (e.g., ICI or co-stimulatory molecule agonist), cancer neoantigen-specific T lymphocytes will be prevented from becoming exhausted/anergic, prevented from differentiation towards a regulatory phenotype, and/or skewed towards being able to i) expand into a higher number of effector T lymphocytes (improved proliferation capacity), and/or ii) be more potent effector cells (improved anti-cancer efficacy).

Immunomodulatory Compound(s) During Ex Vivo T Lymphocyte Activation and/or Expansion As represented by Step (b) in administration routes A, B and C in FIG. 1, adding immunomodulatory compound(s) to the ex vivo activation/expansion of the primed cancer neoantigen-specific T lymphocytes in the TVAX Immunotherapy or other adoptive cell transfer therapy will result in a more potent anti-cancer effector T lymphocyte infusion product. The immunomodulatory compound(s) will prevent T lymphocyte exhaustion and anergy and/or result in additional stimulation during the culture period, which leads to a higher number of effector T lymphocytes and/or the production of cancer neoantigen-specific effector T lymphocytes that have greater potency.

Immunomodulatory Compound(s) Co-Infusion During Adoptive T Cell Transfer

As represented by Step (c) in administration routes A, B and C in FIG. 1, co-infusion of immunomodulatory compound(s) during the adoptive cell transfer of effector T lymphocytes can result in augmented anti-cancer efficacy in the TVAX Immunotherapy or other adoptive cell transfer therapy. The immunomodulatory compound(s) can lead to i) higher number and ii) extended presence of cancer neoantigen-specific effector T lymphocytes in the body, particularly within cancer tissue. Moreover, the infused T lymphocytes are prevented from becoming exhausted and/or anergic.

Immunomodulatory Compound(s) Post Adoptive T Cell Transfer

As represented by Step (d) in administration routes A, B and C in FIG. 1, immunomodulatory compound(s) can be delivered once or several times following adoptive cell transfer of T lymphocytes in the TVAX Immunotherapy or other adoptive cell transfer therapy. This will lead to augmented anti-cancer efficacy Similar to what was described above with respect to co-infusion, the immunomodulatory compound(s) can lead to i) higher number and ii) extended presence of cancer neoantigen-specific effector T lymphocytes in the body, particularly in cancer tissue. Moreover, the infused T lymphocytes are prevented from becoming exhausted and/or anergic.

Other Uses of Immunomodulatory Compounds(s)

Alternative adoptive T cell immunotherapy preparative and/or preconditioning treatments (such as lymphodepletion and/or irradiation) as well as co-treatment with oncolytic virus are other treatment combinations that can be incorporated into a treatment schedule that involves the use of immunomodulatory compounds in the TVAX Immunotherapy or other adoptive cell transfer therapy.

5. ONCOLYTIC VIRUS THERAPY

Oncolytic viruses are viruses that accumulate in cancer cells and replicate in cancer cells. By virtue of their replication in cancer cells and with the optional delivery of therapeutic agents encoded by the oncolytic virus, cancer cells are lysed. The effect of viral infection of cancer tissue is that the cancer shrinks and is sometimes eliminated. As part of this infective process, an inflammatory response is generated and the immunosuppressive cancer microenvironment is converted to an immunostimulatory environment.

Agents that convert cancer tissue into a pro-inflammatory environment promote cancer cell killing by T lymphocytes. Viruses are strong immunogens and have the capacity to activate the immune system. As a result of viral infection, pro-inflammatory cytokines are released by the infected cells and by activated immune cells. Viral infection leads to generation of pathogen-associated molecular patterns (PAMPs) and danger-associated molecular patterns (DAMPs). Virus-induced type 1 interferons stimulate the activity and co-stimulatory potency of antigen presenting dendritic cells and result in the production of additional inflammatory cytokines and chemokines, which leads to further activation and enhancement of both the innate as well as the adaptive immune response.

As a consequence of the host response to viral infection, the cancer microenvironment is transformed from an immunosuppressive state to an immunostimulatory state. The induced inflammatory response within the cancer supports the development and sustainability of a cytolytic cancer neoantigen-specific T lymphocyte response.

Oncolytic viruses effect treatment by colonizing or accumulating and/or replicating in cancer cells; including primary cancer cells, metastatic cancer cells and circulating cancer cells. In many cases, cancer selectivity is an inherent property of the oncolytic virus, exemplified by vaccinia viruses and other oncolytic viruses. Also, many oncolytic viruses such as vaccinia viruses have a broad host and cell type range and can be further engineered (e.g., by deletion of thymidine kinase) to enhance cancer cell-specific replication. Vaccinia virus can accumulate in immune privileged cells or immune privileged tissues, including primary cancers and/or cancer metastases.

Oncolytic viruses for use in the combinations, compositions, use or methods provided herein are well known to one of skill in the art. Therapeutic oncolytic viruses include, but are not limited to, vaccinia viruses, reovirus, measles viruses, mumps virus, adenoviruses and herpes viruses, vesicular stomatitis virus, newcastle disease virus, parvovirus, poliovirus, coxsackie virus, sindbis virus, seneca valley virus, maraba virus and other oncolytic viruses.

Vaccinia virus strains have been shown to specifically colonize solid cancers, while not infecting other organs and tissues. Vaccinia viruses and related viruses include strains selected from among Lister, Western Reserve (WR), Copenhagen (Cop), Bern, Paris, Tashkent, Tian Tan, Wyeth (DRYVAX), IHD-J, IHD-W, Brighton, Ankara, CVA382, Modified Vaccinia Ankara (MVA), Dairen I, LC16m8, LC16M0, LIVP, ACAM2000, WR 65-16, Connaught, New York City Board of Health (NYCBH), EM-63 and NYVAC strain. Exemplary of such viruses are as JX594 and derivatives thereof, WO-12 and derivatives thereof, and the GL-ONC1 (i.e., GLV-1h68) and derivatives thereof, and clonal strains of LIVP and Copenhagen.

Included are clonal strains of each oncolytic virus, as well as those containing heterologous nucleic acid. Oncolytic viruses also include viruses that have been genetically altered to attenuate their virulence, improve their safety profile and enhance their cancer specificity by virtue of having been equipped with additional genes. Generally, the one or more heterologous DNA molecules are inserted into a non-essential region of the virus genome. For example, the one or more heterologous DNA molecules are inserted into a locus of the virus genome that is non-essential for replication in proliferating cells, such as cancer cells. Insertion sites are known in the art.

Heterologous nucleic acids include those encoding a therapeutic gene product, and/or a cancer (neo)antigen, and/or a reporter gene, and/or promoter or regulatory region. Heterologous gene product is selected from among an anti-cancer agent, an anti-metastatic agent, a cancer (neo) antigen, an anti-angiogenic agent, an immunomodulatory molecule or an antigen, a cell matrix degradative gene, genes for tissue regeneration and reprogramming human somatic cells to pluripotency, enzymes that modify a substrate to produce a detectable product or signal or are detectable by antibodies, proteins that can bind a contrasting agent, genes for optical imaging or detection, genes for PET imaging and genes for MRI imaging. The heterologous gene product can be a therapeutic agent selected from among a hormone, a growth factor, a cytokine, a chemokine, a costimulatory molecule, ribozymes, a transporter protein, a single chain antibody, such as an anti-VEGF or anti-VEGFR, or anti-EGFR antibody, or antibodies (agonistic or antagonistic) against immune modulating proteins, an antisense or ds RNA or other RNA product, a prodrug converting enzyme, an siRNA, a microRNA, a toxin, an anti-cancer oligopeptide, a mitosis inhibitor protein, an antimitotic oligopeptide, an anti-cancer polypeptide antibiotic, an angiogenesis inhibitor, a cancer suppressor, a cytotoxic protein, a cytostatic protein or a TLR agonist.

The oncolytic viruses provided herein can be modified to express one or more antigens. Exemplary antigens include, but are not limited to, cancer-specific (neo)antigens, cancer-associated antigens, tissue-specific antigens, bacterial antigens, viral antigens, yeast antigens, fungal antigens, protozoan antigens, parasite antigens and mitogens.

Oncolytic viruses provided herein can be produced by methods known to one of skill in the art. The resulting oncolytic viruses provided herein can be used in therapeutic and diagnostic applications.

The virus is propagated in host cells, quantified and prepared for storage before finally being prepared to use in the methods described herein. The virus can be propagated in suitable host cells to enlarge the stock, the concentration of which is then determined. In some examples, the infectious titer is determined, such as by plaque assay. The total number of viral particles also can be determined. The viruses are stored under conditions that promote stability and integrity of the virus, such that loss of infectivity over time is minimized. In some examples, a large amount of virus is produced and stored in small aliquots of known concentration that can be used for multiple procedures over an extended period of time. Conditions that are most suitable for various viruses will differ, and are known in the art, but typically include freezing or drying, such as by lyophilization. The viruses can be stored at a concentration of $10^5$-$10^{10}$ pfu/mL, for example, $10^7$-$10^9$ pfu/mL, such as at least or about or $10^6$ pfu/mL, $10^7$ pfu/mL, $10^8$ pfu/mL or $10^9$ pfu/mL. Immediately prior to use in the methods provided herein, the stored viruses are reconstituted (if dried for storage) and diluted in an appropriate medium or solution.

Provided are compositions for use in the processes of the invention, combinations and kits that contain therapeutic oncolytic viruses, particularly therapeutic oncolytic viruses, and methods of treatment by administering or using the compositions. An oncolytic virus contained in a pharmaceutical composition, combination or kit can include any oncolytic virus provided herein.

Provided herein are pharmaceutical compositions for use in the processes of the invention containing an oncolytic virus provided herein and a suitable pharmaceutical carrier. A pharmaceutically acceptable carrier includes a solid, semi-solid or liquid material that acts as a vehicle carrier or medium for the oncolytic virus. Pharmaceutical compositions provided herein can be formulated in various forms, for example in solid, semi-solid, aqueous, liquid, powder or lyophilized form. Exemplary pharmaceutical compositions containing an oncolytic virus provided herein include, but are not limited to, sterile injectable solutions, sterile packaged powders, eye drops, tablets, pills, powders, lozenges, sachets, cachets, elixirs, suspensions, emulsions, solutions, syrups, aerosols (as a solid or in a liquid medium), ointments, soft and hard gelatin capsules, and suppositories.

The compositions, may contain a biocompatible lipid and/or lipid-treated oncolytic virus, typically are emulsions. Also provided are lipid-treated therapeutic oncolytic viruses. Lipids include any known to those of skill in the art that can be administered systemically.

Other components in the compositions, including tonicity modifiers, pH adjusters and other such components. Exemplary tonicity modifiers include glycerin, sodium chloride, potassium chloride, mannitol, sucrose, lactose, fructose, maltose, dextrose, dextrose anhydrous, xylitol, sorbitol, propylene glycol, polyoxyethylated hydrocarbons, and C6-C20 saturated and unsaturated aliphatic acids.

The compositions and/or methods provide the oncolytic viruses whereby the infectivity and/or persistence of the oncolytic virus is increased. It is increased such by virtue of increased half-life and/or changes to the virus that protect it from the immune system or enhance interaction and/or uptake by target cells, such as cells that are the target of therapy with therapeutic oncolytic viruses. Target cells include, but are not limited to, cancer cells, circulating cancer cells and metastasizing cancer cells. Target cells include cells in subjects to whom the composition is administered and also include, in vitro cell lines, and ex vivo cells, including cells for T lymphocyte therapy, stem cells and other such cells.

The compositions can be formulated for direct administration. They can be formulated for local or systemic injection, such as intravenous administration.

Kits can include one or more pharmaceutical compositions or combinations provided herein, and one or more components, such as instructions for use, a device for administering the pharmaceutical composition or combination to a subject, a device for administering a therapeutic or diagnostic compound to a subject or a device for detecting a virus in a subject.

In the methods, the compositions can be administered systemically, regionally and/or directly into the malignancy, either as infusion or direct injection; for the combinations the compositions can be administered by the same or different routes. In particular embodiments, the composition(s) is(are) administered intravenously or intraperitoneally.

The oncolytic viruses may be administered in multi-dose and single dosage amounts, including, but not limited to between or about between $1 \times 10^5$ and $1 \times 10^{12}$ pfu, $1 \times 10^6$ to $1 \times 10^{10}$ pfu, $1 \times 10^7$ to $1 \times 10^{10}$ pfu, each inclusive, such as at least or about at least or $1 \times 10^6$, $1 \times 10^7$, $1 \times 10^8$, $1 \times 10^9$, $2 \times 10^9$, $3 \times 10^9$, $4 \times 10^9$, $5 \times 10^9$ pfu, $1 \times 10^{10}$ pfu, $2 \times 10^{10}$ pfu, $3 \times 10^{10}$ pfu, $4 \times 10^{10}$ pfu.

The oncolytic virus may be administered in combination with an agent that modulates or alters or improves a property of the oncolytic virus, such as an agent that increases infectivity of the oncolytic virus. These include agents that alter the immune response to the oncolytic virus so that less is cleared upon administration. Additional agents include complement inhibitors, such as any agent that inhibits complement activation or the activity of any protein in a complement pathway, such as, inhibition of the activity of any of C1, C2, C3, C4, C5, C5a, C5aR, C3aR, Factor B, Factor P, C1q and MBP. Such agents are known to those of skill in the art, and include, for example, include antibodies specific for one or more of these proteins, such as anti-C5 antibodies. Exemplary inhibitors include, for example, cobra venom factor (CVF), heparin, TA 106, TNX-234, anti-properdin, C1-INH, a compstatin or derivative or analog thereof, soluble CR1, K76COOH, eculizumab, pexelizumab, TSA12/22, MSA12/22, ARC 1005, TNX-558, NOX-D19, PMX-53, PMX-201, PMX-205, neutrazumab, and variants, analogs or derivatives thereof that inhibit a complement activity.

Further disclosure of oncolytic virus technology may be found in PCT Application WO 2015/103438 and WO 2012/142529, the disclosures of which are hereby incorporated by reference in their entirety.

6. IMMUNOMODULATORY COMPOUNDS

Numerous immunomodulatory pathways exist that influence the proliferative abilities, the differentiation, and/or activity of T lymphocytes. Generally, those pathways are described to be either inhibiting effector functions of T lymphocytes through targeting immune checkpoint proteins, or augmenting effector functions through activation of co-stimulatory proteins that are expressed by the T lymphocytes and/or through activation of immune accessory cells, such as macrophages, NK cells and dendritic cells.

Co-inhibitory molecules such as CTLA-4 and PD-1 are induced in activated T lymphocytes and binding of these proteins to their ligands results in inhibition of the T lymphocyte effector functions. Antibodies that block the interaction of those receptors and their ligands (checkpoint-inhibitors) are thought to prevent these inhibitory effects and thereby augment the therapeutic effects of T lymphocytes against cancer cells.

Co-stimulatory proteins include constitutively expressed surface receptors such as CD28 and CD27 and others whose expression is induced upon antigen priming of the T lymphocyte. OX40 (CD134), ICOS (CD278), GITR (CD357), and 4-1BB (CD137) are among those inducible receptors.

Agonistic (stimulating) antibodies against these co-stimulatory proteins are thought to enhance effector T lymphocyte functions and thereby improve therapeutic effects against cancer.

As a consequence of the use of immunomodulatory compounds administered to patients, cancer neoantigen-specific T lymphocytes will be prevented from becoming exhausted/anergic, prevented from differentiation towards a regulatory phenotype, and/or skewed towards being able to i) expand into a higher number of effector T lymphocytes (better proliferation capacity), and/or ii) be more potent effector cells (better anti-cancer efficacy). The immunomodulatory compound(s) can therefore lead to i) higher number and ii) extended presence of cancer neoantigen-specific effector T lymphocytes. Moreover, the infused T lymphocytes are prevented from becoming exhausted and/or anergic. Consequently, co-infusion of immunomodulatory compound(s) during and/or after the adoptive T cell therapy can result in augmented anti-cancer efficacy. Post adoptive T cell immunotherapy, immunomodulatory compound(s) can be injected once or several times.

Adding immunomodulatory compound(s) to the ex vivo activation/expansion of T lymphocytes can result in a more potent anti-cancer T lymphocyte immunotherapy product. The immunomodulatory compound(s) can prevent T lymphocyte exhaustion and anergy and/or result in additional stimulation which leads to a higher number of effector T lymphocytes and/or the production of T lymphocytes that have greater potency, thereby generating a higher overall number effector T lymphocytes.

Inhibitory pathways can be attacked by immunomodulatory compounds that are known as immune checkpoint inhibitors. These compounds block the interaction of immune checkpoint proteins and their ligands; whereas compounds that activate co-stimulatory molecules on T lymphocytes act as agonists. Therefore, immunomodulatory compounds bind to proteins on T lymphocytes or other cells (such as cancer cells, macrophages, antigen-presenting cells (dendritic cells), MSDCs, or NK cells) or ligands thereof, which results in the modulation of effector cell T lymphocyte and effector T lymphocyte-activated bystander cell activity. Immunological targets that bind such compounds include, but are not limited to CTLA4, CD28, CD80 (B7-1), CD86 (B7-2), PD-1, PD-L1 (B7-H1), PD-L2 (B7-DC), 4-1BB (CD137/TNFRSF9), 4-1BB ligand, OX40 (CD134/TNFRSF4), OX40 ligand (CD252/TNFSF4) ICOS, ICOS ligand, GITR (CD357/TNFRSF18), GITR ligand (TNFSF18), CD27, CD70, TNFRSF25 (DR3), TL1A (TNFSF15), CD40 (TNFRSF5), CD40L (TNFSF5), HVEM (TNFRSF14), CD160, LIGHT (HVEML/TNFSF14), BTLA, Siglecs, LAG3, TIM3 (HAVCR2), phosphatidylserine, galectins, B7-H3 (CD276), B7-H4 (VTCN1), VISTA, HHLA2, TMIGD2, Butyrophilin-like proteins, BTNL2, TIGIT, CD155 (PVR), CD226 (DNAM1), CD96, CD112 (PVRL2/nectin2), CD113 (PVRL3/nectin3), nectins CD25, CD30, VEGF, VEGFR, Neuropilin, IDO, TGF□, CD39, CD73, Adenosine, ADORA2A (A2A), IL-10, IL-27, CXCR4, CXCL12 KIRs (e.g., KIR2DL1, KIR2DL2, KIR2DL3), C-type lectins (e.g., NKG2A, NKG2D), MICA, MICB, ILT/LIR protein family members, CD244, CD48 CSF1R, SIRPA (CD172a), CD47 and TLR (TLR1-11).

Immunomodulatory compounds include, but are not limited to, Ipilimumab, Tremelimumab, Galiximab, TGN1412, Pembrolizumab (MK-3475, Lambrolizumab), Nivolumab (ONO-4538, MDX1106, BMS936558), Atezolizumab (MPDL3280A), MEDI4736, Avelumab (MSB0010718C), PDR001, Pidilizumab (CT-011), MEDI0680 (AMP-514), AUNP-12, BMS-936559 (MDX1105), Urelumab, PF-05082566, BMS-663513, MEDI6383, MEDI6469, MOXR0916, GSK3174998, GSK3359609, TRX518, Varlilumab (CDX1127), CP-870893, BMS-986016, IMP321, Bavituximab, MGA271, Bevacizumab, MNRP1685A, INCB024360, Galunisertib, Ulocuplumab, BKT140, Larilumab, IPH2101, IPH2201, Emactuzumab (RG7155), CC-90002, and the TLR-agonists; triacyl lipoproteins, heat shock proteins, peptidoglycans, lipoproteins, HMGB1 (high mobility group box 1-amphoterin), lipoteichoic acid, self dsRNA, viral dsRNA, fibrinogen, lipopolysaccharides, heparin sulfate, RSV fusion protein, hyaluronic acid, paclitaxel, flagellin, triacyl lipoproteins, zymosan, self DNA, viral or bacterial DNA and profilin.

Provided are compositions for use in the processes of the invention, combinations and kits that contain immunomodulatory compounds, and methods of treatment by administering or using the compositions. An immunomodulatory compound contained in a pharmaceutical composition, combination or kit can include any immunomodulatory compound provided herein.

Provided herein are pharmaceutical compositions for use in the processes of the invention containing an immunomodulatory compound provided herein and a suitable pharmaceutical carrier. A pharmaceutically acceptable carrier includes a solid, semi-solid or liquid material that acts as a vehicle carrier or medium for the immunomodulatory compound. Pharmaceutical compositions provided herein can be formulated in various forms, for example in solid, semi-solid, aqueous, liquid, powder or lyophilized form. Exemplary pharmaceutical compositions containing an immunomodulatory compound provided herein include, but are not limited to, sterile injectable solutions, sterile packaged powders, eye drops, tablets, pills, powders, lozenges, sachets, cachets, elixirs, suspensions, emulsions, solutions, syrups, aerosols (as a solid or in a liquid medium), ointments, soft and hard gelatin capsules, and suppositories.

Other components in the compositions, including tonicity modifiers, pH adjusters and other such components. Exemplary tonicity modifiers include glycerin, sodium chloride, potassium chloride, mannitol, sucrose, lactose, fructose, maltose, dextrose, dextrose anhydrous, xylitol, sorbitol, propylene glycol, polyoxyethylated hydrocarbons, and C6-C20 saturated and unsaturated aliphatic acids.

The compositions and/or methods provide the immunomodulatory compound(s) whereby the activity and/or persistence of the immunomodulatory compound(s) is increased. It is increased by virtue of increased half-life and/or changes to the immunomodulatory compound(s) that protect it from the immune system or enhance interaction and/or uptake by target cells, such as cells that are the target of therapy with immunomodulatory compound(s). Target cells include, but are not limited to, T lymphocytes, antigen presenting cells, macrophages, dendritic cells, fibroblasts, stem cells, cancer cells, circulating cancer cells and metastasizing cancer cells. Target cells include cells in subjects to whom the composition is administered and also include, in vitro cell lines, and ex vivo cells, including cells for T cell immunotherapy, stem cells and other such cells.

The compositions can be formulated for direct administration. They can be formulated for local or systemic injection, such as intravenous administration.

Kits can include one or more pharmaceutical compositions or combinations provided herein, and one or more components, such as instructions for use, a device for administering the pharmaceutical composition or combination to a subject, a device for administering a therapeutic or diagnostic compound to a subject or a device for detecting a virus in a subject.

In the methods, the compositions can be administered ex vivo, systemically, regionally, or directly into the malignancy, either as infusion or direct injection; for the combinations the compositions can be administered by the same or different routes. In particular embodiments, the composition(s) is(are) administered ex vivo, intravenously or intraperitoneally.

7. DISEASES THAT COULD BE TREATED IN HUMANS AND NON-HUMAN ANIMALS

Diseases and conditions that can be treated with the processes of the present invention include cancers and proliferative disorders or conditions, including the treatment of cancerous cells, neoplasms, cancers, and metastases. As used herein, cancer is a term for diseases caused by or characterized by any type of malignant cancer, including solid cancers, metastatic cancers, lymphatic cancers, and blood cancers. Exemplary cancers include, but are not limited to, leukemia, lymphoma, pancreatic cancer, lung cancer, ovarian cancer, breast cancer, cervical cancer, bladder cancer, prostate cancer, brain cancer, adenocarcinomas, liver cancer and skin cancer. Exemplary cancers in humans include a bladder cancer, breast cancer, prostate cancer, basal cell carcinoma, biliary tract cancer, bladder cancer, bone cancer, brain and central nervous system cancer (e.g., glioma), adenocarcinomas, lung cancer, cervical cancer, choriocarcinoma, colon and rectum cancer, connective tissue cancer, cancer of the digestive system; cancer of the small intestine and cecum; endometrial cancer, esophageal cancer; eye cancer; cancer of the head and neck; gastric cancer; intra-epithelial neoplasm; kidney cancer; larynx cancer; leukemia; liver cancer; gall bladder cancer lung cancer (e.g., small cell and non-small cell); lymphoma including Hodgkin's and Non-Hodgkin's lymphoma; melanoma; myeloma, neuroblastoma, oral cavity cancer (e.g., lip, tongue, mouth, and pharynx); cancer of the salivary glands; ovarian cancer; pancreatic cancer, retinoblastoma; rhabdomyosarcoma; rectal cancer, renal cancer, cancer of the respiratory system; sarcoma, skin cancer; stomach cancer, testicular cancer, thyroid cancer; uterine cancer, cancer of the urinary system, as well as other carcinomas and sarcomas.

Exemplary cancers commonly diagnosed in dogs, cats, and other pets include, but are not limited to, lymphosarcoma, osteosarcoma, mammary cancers, mastocytoma, brain cancer, melanoma, adenosquamous carcinoma, carcinoid lung cancer, bronchial gland cancer, bronchiolar adenocarcinoma, fibroma, myxochondroma, pulmonary sarcoma, neurosarcoma, osteoma, papilloma, retinoblastoma, Ewing's sarcoma, Wilm's tumor, Burkitt's lymphoma, microglioma, neuroblastoma, osteoclastoma, oral neoplasia, fibrosarcoma, osteosarcoma and rhabdomyosarcoma, genital squamous cell carcinoma, transmissible venereal cancer, testicular cancer, seminoma, Sertoli cell cancer, hemangiopericytoma, histiocytoma, chloroma (e.g., granulocytic sarcoma), corneal papilloma, corneal squamous cell carcinoma, hemangiosarcoma, pleural mesothelioma, basal cell cancer, thymoma, stomach cancer, adrenal gland carcinoma, oral papillomatosis, hemangioendothelioma and cystadenoma, follicular lymphoma, intestinal lymphosarcoma, fibrosarcoma and pulmonary squamous cell carcinoma.

The subjects include humans and non-human animals, particularly domesticated and farm animals and experimental animals, such as, chimpanzees, gorillas, horse, cat, dog, cow, pig, sheep, goat, mouse, rabbit, chicken, rat, and guinea pig.

8. ADOPTIVE T CELL THERAPIES

TVAX Immunotherapy (Previously Called Cancer Antigen Immunotherapy)

Step 1: Vaccination.

The first step in the present invention is the vaccination of patients with antigens from their own malignancy. In patients who have a solid malignancy, at least a portion of the cancer is surgically removed to create a single cell suspension of malignant cells. The surgical specimen is enzymatically digested with enzymes manufactured by various life science products companies. In patients who have hematologic malignancies or solid malignancies with free cells in pleural, pericardial or peritoneal fluid, the malignant cells are obtained from the blood, bone marrow, pleural or pericardial effusion, or ascites fluid. The isolated malignant cells are irradiated to prevent local growth. The cells are stored frozen until the vaccination is performed.

Cancer antigen could also be obtained and delivered in alternative forms, such as a purified protein, DNA or RNA extract of the cancer, a genetically engineered antigen or antigenic peptide or oncolytic virus-infected cancer cells.

In a preferred embodiment, at the time of vaccination, the attenuated malignant cells are combined with an immunologic adjuvant, preferably soluble recombinant human GM-CSF. In the preferred embodiment, the vaccine is administered intradermally to multiple body sites.

Other methods of administration of the immunological adjuvant alone or in combination with other agents that could add to the potency and ease of delivery of the GM-CSF are possible. Also, other immunological adjuvants and/or routes of administration could be used.

Step 2: Isolation of T Lymphocytes.

The second step in TVAX Immunotherapy involves the activation of T lymphocytes from the immunized patients. Local immunization leads to production of primed cancer neoantigen-specific T lymphocytes in lymphoid tissue draining the immunization sites. The primed T lymphocytes are then released from lymphoid tissue into the blood so that they may be carried to the sites of disease activity. Since primed T lymphocytes are released into the blood, peripheral blood provides a reliable source of cancer neoantigen-specific T lymphocyte effector precursors. The preferred method for obtaining the peripheral blood lymphocytes is by apheresis. Alternatively, primed T lymphocytes may be obtained from lymphoid tissue or cancer tissue following immunization.

Step 3: Activation and Proliferation of Cancer Neoantigen-Specific T Lymphocytes.

In the preferred embodiment, the activation and proliferation of T lymphocytes occurs during in vitro cell culture as the result of a cooperative interaction between adherent monocytes and non-adherent T lymphocytes that is facilitated by T lymphocyte activating agents. Peripheral blood mononuclear white blood cells (rich source of T lymphocytes and monocytes) are cultured in cell culture vessels that allow cell attachment in cell culture medium containing autologous serum.

The peripheral blood T lymphocytes are activated in culture with mouse monoclonal anti-CD3 (OKT3) and then stimulated to proliferate by interleukin 2, interleukin 7, interleukin 15 and/or interleukin 21. The stimulus must be capable of stimulating primed T lymphocytes to differentiate into effector T lymphocytes that maintain cancer neoantigen specificity and develop effector activity.

In the preferred embodiment, the stimulated effector cells are stimulated to proliferate in culture using a combination of interleukin 7 and 15. Other cytokines capable of stimulating proliferation of T lymphocytes, such as interleukin 2 and/or interleukin 21, may be added to or substituted for interleukin 7/15.

In an additional/alternative method for stimulation, agonistic immunomodulatory compounds, including but not limited to anti-OX40, anti-ICOS, anti-GITR, anti-CD27, or anti-4-1BB/CD137 compounds (e.g., antibodies and/or aptamers), are used. Another alternative method includes the use of such as ICI. Another alternative method includes the use of other superantigens than anti-CD3 as the T lymphocyte activator.

In yet another additional/alternative method, T lymphocyte subsets are enriched for certain subpopulation(s) (e.g., PD-1pos T lymphocytes, CD137pos T lymphocytes, CD62Llow T lymphocytes and/or CD27pos T lymphocytes).

Or, T lymphocytes can be transformed with nucleic acids including (e.g., sd-rxRNA) that reduce the expression of immune checkpoint inhibitor receptors (e.g., CTLA-4; PD-1).

Step 4: Infusion of Activated T Lymphocytes (Adoptive T Cell Transfer).

After the stimulated cells have been harvested from culture, the cells are infused intravenously. Although the patient generally is infused with about 1010 to 1012 lymphocytes during a period of about 1 to 6 hours, the number of mononuclear cells administered is solely dependent upon the number of cells generated during the proliferation step. Over 1012 autologous lymphocytes have been safely infused into cancer patients. Lymphocytes could also be pre-loaded with oncolytic virus (enhanced delivery). T lymphocyte infusion is generally performed after oncolytic virus injection (systemic, local and/or intratumoral) into the cancer patient, but could also be performed prior to oncolytic virus injection. Moreover, combination with immunomodulatory compound(s) administration is possible, which could be given during and/or after adoptive T cell transfer.

Further disclosure of adoptive T cell therapy processes may be found in U.S. Pat. No. 6,406,699, which is hereby incorporated by reference in its entirety, and references 3-12 below, the disclosures of each are hereby incorporated by reference with respect to such disclosure.

Tumor Infiltrating Lymphocyte (TIL) Therapy

Step 1: Isolation, Activation and Expansion of TILs.

T lymphocytes can be found in most cancers and metastases. Due to the presence of cancer-associated antigens, T lymphocytes specific for these antigens are enriched compared to the total T lymphocyte population of the patient. After surgical removal of cancer tissue, T lymphocytes that are present in the tissue can be isolated. The preferred method of isolating (cancer-associated, antigen-specific) T lymphocytes is by incubation of small cancer fragments in tissue culture containers in the presence of cell culture medium. Lymphocytes (including cancer-specific T lymphocytes) from those cultures are usually harvested after 3-4 weeks of in vitro culture.

In the preferred embodiment, the T lymphocytes derived from cancer tissue are activated in culture with mouse monoclonal anti-CD3 (OKT3) and then stimulated to proliferate by interleukin 2. The stimulus must be capable of stimulating primed T lymphocytes to differentiate into effector T lymphocytes that maintain cancer neoantigen specificity and develop effector activity.

In the preferred embodiment, the stimulated effector cells are proliferated in culture using interleukin 2. Other cytokines capable of stimulating proliferation of T lymphocytes, such as interleukin 7 and/or interleukin 15 and/or interleukin 21, may be substituted for interleukin 2.

In an additional/alternative method for stimulation, agonistic immunomodulatory compounds, including but not limited to anti-OX40, anti-ICOS, anti-GITR, anti-CD27, or anti-4-1BB/CD137 compounds (e.g., antibodies and/or aptamers), are used. Another alternative method includes the use of such as ICI.

In yet another additional/alternative method, T lymphocyte subsets are enriched for certain subpopulation(s) (e.g., PD-1pos T lymphocytes, CD137pos T lymphocytes, and/or CD27pos T lymphocytes).

Or, T lymphocytes can be transformed with nucleic acids including (e.g., sd-rxRNA) that reduce the expression of immune checkpoint inhibitor receptors (e.g., CTLA-4; PD-1).

Step 2: Infusion of Activated T Lymphocytes (Adoptive T Cell Transfer).

After the stimulated cells have been harvested from culture, the cells are infused intravenously. Although the patient generally is infused with about 1010 to 1012 lymphocytes during a period of about 1 to 6 hours, the number of mononuclear cells administered is dependent upon the number of cells generated during the proliferation step. Over 1012 autologous lymphocytes have been safely infused into cancer patients. Lymphocytes could also be pre-loaded with oncolytic virus (enhanced delivery). T lymphocyte infusion is generally performed after oncolytic virus injection (systemic, local and/or intratumoral) into the cancer patient, but could also be performed prior to oncolytic virus injection. Moreover, combination with immunomodulatory compound(s) administration is possible, which could be given during and/or after adoptive T cell transfer.

T Cell Receptor (TCR) Gene Therapy and Chimeric Antigen Receptor (CAR) Engineered T Cell Therapy Step 1: Generation of Genetically Engineered T Lymphocytes.

There are numerous procedures and protocols on how to genetically engineer and expand autologous or allogeneic T lymphocytes ex vivo. The product of these procedures and protocols are T lymphocytes expressing (pre-) defined TCR, which recognize cancer antigen epitopes when presented by MHC molecules, or CAR expressing T lymphocytes that bind and are activated by defined antigens, which are present on the cancer cell surface.

Step 2: Infusion of Genetically Engineered T Lymphocytes.

Genetically engineered T lymphocytes that have been expanded ex vivo and harvested, are infused into the patient. T lymphocyte infusion is generally performed after oncolytic virus injection (systemic, local and/or intratumoral) into the cancer patient, but could also be performed prior to oncolytic virus injection. Moreover, combination with immunomodulatory compound(s) administration is possible, which could be given during and/or after adoptive T cell transfer.

9. TREATMENT BENEFITS WITH OTHER AGENTS

Also provided are combinations of agents as an adjunct to viral administration and adoptive T cell immunotherapy. The additional active agent such as, but not limited to a therapeutic compound, an agent that increases oncolytic virus infectivity, an agent that extends and/or increases oncolytic virus or T lymphocyte presence, spread, and/or replication inside the cancer tissue, or an agent or compound for modulation of gene expression of endogenous or heterologous genes encoded by the oncolytic virus. Additional active agents include agents that modulate or alter or improve properties of the oncolytic virus and/or and adoptive T cell immunotherapy as well as agents that modulate or alter the immune system.

Thus, provided herein are methods of administering to a subject one or more therapeutic compounds that can act in conjunction with the oncolytic virus and/or adoptive T cell immunotherapy to increase the proliferation, cancer cell killing, or immune response enhancing properties of an oncolytic virus and/or the adoptive T cell immunotherapy. Also provided herein are methods of administering to a subject one or more therapeutic compounds that can act in conjunction with the oncolytic virus and/or adoptive T cell immunotherapy to decrease the proliferation, toxicity, or cell killing properties of an oncolytic virus and/or adoptive cell therapy. Therapeutic compounds to be administered can be any of those provided herein or in the art. The target cells can be treated in vivo, ex vivo and/or in vitro as described herein.

Cyclophosphamide (CPA) alone or in combination with fludarabine, temozolomide or other lymphodepleting agents may be used as an adjunct to viral administration and/or adoptive T cell therapy. CPA is an alkylating agent and a classic chemotherapeutic compound and induces genotoxic stress, apoptosis and/or cell cycle arrest. CPA functions to promote oncolytic virotherapy and adoptive T cell immunotherapy via several mechanisms.

CPA (with or without combination of local cancer tissue or whole-body irradiation) can enhance anticancer activity of adoptively transferred immune cells and CPA prevents loss of lytic activity via lymphodepletion (e.g., of regulatory T lymphocytes) resulting in extended effector T lymphocyte activity in vivo.

Oncolytic adenovirus given together with metronomic CPA increased cytotoxic T lymphocytes and induced Th1 type immunity on a systemic level in most cancer patients tested. Moreover, CPA enhances adaptive anticancer immunity induced by oncolytic viruses. Greater cancer infection and greater duration of colonization of cancers of vaccinia virus in combination with cyclophosphamide treatment has been demonstrated in preclinical experiments. Reported studies confirm that CPA can enhance viral replication of oncolytic viruses and enhance adaptive anti-cancer immunity in vivo, thus resulting in better efficacy. In summary, CPA has emerged as a clinically feasible agent that can suppress regulatory T lymphocytes and allow more effective induction of anti-cancer immune responses, in the setting of cancer vaccines and other immunotherapeutic strategies.

Any therapeutic or anti-cancer agent can be used as the second therapeutic or anti-cancer agent in the combined cancer treatment methods provided herein. The methods can include administering one or more therapeutic compounds to the subject in addition to administering an oncolytic virus and/or adoptive T cell immunotherapy or a plurality thereof to a subject. Therapeutic compounds can act independently, or in conjunction with the oncolytic virus and/or adoptive T cell immunotherapy, for anti-cancer therapeutic effects.

Therapeutic compounds that can act independently include any of a variety of known chemotherapeutic compounds that can inhibit cancer growth, inhibit metastasis growth and/or formation, decrease the size of a cancer or metastasis, eliminate a cancer or metastasis, without reducing the ability of a oncolytic virus and/or adoptively transferred effector T lymphocytes to accumulate in a cancer, replicate in the cancer, and cause or enhance an anti-cancer immune response in the subject.

Therapeutic compounds that act in conjunction with the oncolytic viruses and/or adoptive T cell immunotherapy include, for example, compounds that alter the expression of the oncolytic viruses or compounds that can interact with a virally-expressed gene, or compounds that can inhibit virus proliferation, including compounds toxic to the oncolytic virus. Therapeutic compounds that can act in conjunction with the oncolytic virus and/or adoptive T cell immunotherapy include, for example, therapeutic compounds that increase the proliferation, cancer cell killing or immune response eliciting properties of an oncolytic virus and/or adoptive T cell immunotherapy, and also can include, for example, therapeutic compounds that decrease the proliferation, toxicity or cell killing properties of an oncolytic virus. Optionally, the therapeutic agent can exhibit or manifest additional properties, such as, properties that permit its use as an imaging agent, as described elsewhere herein.

Therapeutic compounds also include, but are not limited to, chemotherapeutic agents, nanoparticles, radiation therapy, siRNA molecules, enzyme/pro-drug pairs, photosensitizing agents, toxins, microwaves, a radionuclide, an angiogenesis inhibitor, a mitosis inhibitor protein (e.g., cdc6), an anti-cancer oligopeptide (e.g., antimitotic oligopeptides, high affinity cancer-selective binding peptides), a signaling modulator, anti-cancer antibiotics, immunomodulatory compounds or a combination thereof.

Exemplary photosensitizing agents include, but are not limited to, for example, indocyanine green, toluidine blue, aminolevulinic acid, texaphyrins, benzoporphyrins, phenothiazines, phthalocyanines, porphyrins such as sodium porfimer, chlorins such as tetra(m-hydroxyphenyl)chlorin or tin(IV) chlorin e6, purpurins such as tin ethyl etiopurpurin, purpurinimides, bacteriochlorins, pheophorbides, pyropheophorbides or cationic dyes. In one example, a vaccinia virus, such as a vaccinia virus provided herein, and/or adoptive T cell therapy is administered to a subject having a cancer or cancer metastasis in combination with a photosensitizing agent.

Radionuclides, which depending upon the radionuclide, amount and application can be used for diagnosis and/or for treatment. They include, but are not limited to, for example, a compound or molecule containing Phosphorus, Cobalt, Yttrium, Technitium, Palladium, Ruthenium, Indium, Lutetium, Iodine, Iodine, Cesium, Samarium, Rhenium, Rhenium, Iridium, Gold, Astatine, Bismuth or Bismuth. In one example, a vaccinia virus, such as a vaccinia virus provided herein, and/or adoptive T cell immunotherapy is administered to a subject having a cancer or cancer metastasis in combination with a radionuclide.

Toxins include, but are not limited to, chemotherapeutic compounds such as, but not limited to, 5-fluorouridine, calicheamicin and maytansine. Signaling modulators include, but are not limited to, for example, inhibitors of macrophage inhibitory factor, toll-like receptor agonists and stat 3 inhibitors. In one example, a vaccinia virus, such as a vaccinia virus provided herein, and/or adoptive T cell immunotherapy is administered to a subject having a cancer or cancer metastasis in combination with a toxin or a signaling modulator.

Combination therapy between chemotherapeutic agents and therapeutic oncolytic viruses and/or adoptive T cell immunotherapy can be effective/curative in situations when single agent treatment is not effective. Chemotherapeutic compounds include, but are not limited to, alkylating agents such as thiotepa, temozolomide and cyclophosphamide; alkyl sulfonates such as busulfan, improsulfan and piposulfan; aziridines such as benzodepa, carboquone, meturedepa and uredepa; ethylenimine and methylmelamines, including altretamine, triethylenemelamine, triethylenephosphoramide, triethylenethiophosphoramide and trimethylmelamine nitrogen mustards such as chlorambucil, chlornaphazine, chlorophosphamide, estramustine, ifosfamide, mechlorethamine, mechlorethamine oxide hydrochloride, melphalan, novobiocin, phenesterine, prednimustine, trofosfamide, uracil mustard; nitrosoureas such as carmustine, chlorozotocin, fotemustine, lomustine, nimustine, ranimustine; antibiotics such as aclacinomycins, actinomycin, anthramycin, azaserine, bleomycins, cactinomycin, calicheamicin, carubicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatrexate; defosfamide; demecolcine; diaziquone; eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; polysaccharide-K; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacyto sine; cyto sine arabino side; cyclopho sphamide; thiotepa; taxoids, e.g., paclitaxel and docetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; Navelbine; Novantrone; teniposide; daunomycin; aminopterin; Xeloda; ibandronate; CPT11; topoisomerase inhibitor RFS 2000; difluoromethylornithine (DMFO); retinoic acid; esperamycins; capecitabine; and pharmaceutically acceptable salts, acids or derivatives of any of the above. Also included are anti-hormonal agents that act to regulate or inhibit hormone action on cancers such as anti-estrogens including for example tamoxifen, raloxifene, aromatase inhibiting 4(5)-imidazoles, 4-hydroxytamoxifen, trioxifene, keoxifene, LY117018, onapristone and toremifene (Fareston); and antiandrogens such as flutamide, nilutamide, bicalutamide, leuprolide and goserelin; and pharmaceutically acceptable salts, acids or derivatives of any of the above. Such chemotherapeutic compounds that can be used herein include compounds whose toxicities preclude use of the compound in general systemic chemotherapeutic methods. Chemotherapeutic agents also include new classes of targeted chemotherapeutic agents such as, for example, imatinib (sold by Novartis under the trade name Gleevec in the United States), gefitinib (developed by Astra Zeneca under the trade name Iressa) and erlotinib. Particular chemotherapeutic agents include, but are not limited to, cisplatin, carboplatin, oxaliplatin, DWA2114R, NK121, IS 3 295, and 254-S vincristine, prednisone, doxorubicin and L-asparaginase; mechlorethamine, vincristine, procarbazine and prednisone (MOPP), cyclophosphamide, vincristine, procarbazine and prednisone (C-MOPP), bleomycin, vinblastine, gemcitabine and 5-flurouracil. Exemplary chemotherapeutic agents are, for example, cisplatin, carboplatin, oxaliplatin, DWA2114R, NK121, IS 3 295, and 254-S. In a non-limiting example, a vaccinia virus, such as a vaccinia virus provided herein, is administered to a subject having a cancer or cancer metastasis in combination with a platinum coordination complex, such as cisplatin, carboplatin, oxaliplatin, DWA2114R, NK121, IS 3 295, and 254-S.

Cancers and cancer metastases can be a monotherapy-resistant cancer such as, for example, one that does not respond to therapy with oncolytic virus and/or adoptive cell T immunotherapy alone or an anti-cancer agent alone, but that does respond to therapy with a combination of oncolytic virus and/or adoptive T cell immunotherapy and an anti-cancer agent. Typically, a therapeutically effective amount of oncolytic virus and/or adoptive T cell immunotherapy is systemically administered to the subject and the oncolytic virus and/or adoptively transferred T lymphocytes localize and accumulate in the cancer. As another example, the cancer is treated with radiotherapy and/or chemotherapy to produce a condition of minimal residual disease in a disease that is particularly radiation and/or chemotherapy sensitive but where neither radiation nor chemotherapy is curative. Adoptive T cell immunotherapy alone or in combination with oncolytic virotherapy can then be delivered to eliminate remaining cancer cells.

Exemplary anti-cancer antibiotics include, but are not limited to, anthracyclines such as doxorubicin hydrochloride (adriamycin), idarubicin hydrochloride, daunorubicin hydrochloride, aclarubicin hydrochloride, epirubicin hydrochloride and pirarubicin hydrochloride, phleomycins such as phleomycin and peplomycin sulfate, mitomycins such as mitomycin C, actinomycins such as actinomycin D, zinostatinstimalamer and polypeptides such as neocarzinostatin. In one example, a vaccinia virus, such as a vaccinia virus provided herein, is administered to a subject having a cancer or cancer metastasis in combination with an anti-cancer antibiotic.

In one example, nanoparticles can be designed such that they carry one or more therapeutic agents provided herein. Additionally, nanoparticles can be designed to carry a molecule that targets the nanoparticle to the cancer cells, oncolytic virus infected cells and/or the infused T lymphocytes. In one non-limiting example, nanoparticles can be coated with a radionuclide and, optionally, an antibody immunoreactive with a cancer-associated antigen.

Therapeutic compounds that can act in conjunction with the oncolytic virus and/or the adoptive T cell immunotherapy to increase the proliferation, cancer cell killing or immune response eliciting properties of an oncolytic virus and/or adoptive T cell immunotherapy are compounds that can alter gene expression, where the altered gene expression can result in an increased killing of cancer cells or an increased anti-cancer immune response in the subject. A gene expression-altering compound can, for example, cause an increase or decrease in expression of one or more genes, including endogenous viral genes and/or exogenous viral genes, genes of the adoptively transferred T lymphocytes, and/or genes of cells that are present in cancer tissue (e.g., cancer cells, stromal cells, including but not limited to, cancer associated fibroblasts, endothelial cells, dendritic cells, macrophages, myeloid-derived suppressor cells). For example, a gene expression-altering compound can induce or increase transcription of a gene in an oncolytic virus and/or effector T lymphocytes such as an exogenous gene that can cause cell lysis or cell death that can provoke an immune response that can catalyze conversion of a prodrug-like compound, or that can inhibit expression of a cancer cell gene. Any of a wide variety of compounds that can alter gene expression are known in the art, including IPTG, RU486, and epigenetic modulators. Exemplary genes whose expression can be up-regulated include proteins and RNA molecules, including toxins, enzymes that can convert a prodrug to an anti-cancer drug, cytokines, transcription regulating proteins, siRNA and ribozymes. Any of a variety of compounds that can reduce or inhibit gene expression can be used in the methods provided herein, including siRNA compounds, transcriptional inhibitors or inhibitors of transcriptional activators. Exemplary genes whose expression can be down-regulated include proteins and RNA molecules, including viral and/or adoptive T cell therapy proteins or RNA that suppress lysis, nucleotide synthesis or proliferation, and cellular proteins or RNA molecules that suppress cell death, immunoreactivity, lysis, or viral and/or adoptive cell therapy replication.

In another example, therapeutic compounds that can act in conjunction with the oncolytic virus and/or adoptive T cell therapy to increase the proliferation, cancer cell killing, or immune response eliciting properties of an oncolytic virus and/or adoptive T cell immunotherapy are compounds that can interact with an expressed gene product, and such interaction can result in an increased killing of cancer cells or an increased anti-cancer immune response in the subject. A therapeutic compound that can interact with an expressed gene product can include, for example a prodrug or other compound that has little or no toxicity or other biological activity in its subject-administered form, but after interaction with a virally expressed gene product, the compound can develop a property that results in cancer cell death, including but not limited to, cytotoxicity, ability to induce apoptosis, or ability to trigger an immune response. Once the enzyme is introduced into the cancer cells, an inactive form of a chemotherapy drug (i.e., a prodrug) is administered. When the inactive prodrug reaches the cancer cells, the enzyme converts the prodrug into the active chemotherapy drug, so that it can kill the cancer cell. Thus, the treatment is targeted only to cancer cells. The prodrug can be administered concurrently with, or sequentially to, the oncolytic virus and/or adoptive T cell immunotherapy. A variety of prodrug-like substances are known in the art and an exemplary set of such compounds are disclosed elsewhere herein, where such compounds can include gancyclovir, 5-fluorouracil, 6-methylpurine deoxyriboside, cephalosporin-doxorubicin, 4-[(2-chloroethyl)(2-mesyloxyethyl)amino]benzoyl-L-glutamic acid, acetaminophen, indole-3-acetic acid, CB 1954, 7-ethyl-10-[4-(1-piperidino)-1-piperidino]carbonyloxycamptothecin, bis-(2-chloroethyl)amino-4-hydroxyphenyl-aminomethanone 28, 1-chloromethyl-5-hydroxy-1,2-dihydro-3H-benz[e]indole, epirubicin-glucuronide, 5'-deoxy-5-fluorouridine, cytosine arabinoside, linamarin, and a nucleoside analogue (e.g., fluorouridine, fluorodeoxyuridine, fluorouridine arabinoside, cytosine arabinoside, adenine arabinoside, guanine arabinoside, hypoxanthine arabino side, 6-mercaptopurineriboside, theoguanosine riboside, nebularine, 5-iodouridine, 5-iododeoxyuridine, 5-bromodeoxyuridine, 5-vinyldeoxyuridine, 9-[(2-hydroxy) ethoxy]methylguanine (acyclovir), 9-[(2-hydroxy-1-hydroxymethyl)-ethoxy]methylguanine (DHPG), azauridien, azacytidine, azidothymidine, dideoxyadenosine, dideoxycytidine, dideoxyinosine, dideoxyguanosine, dideoxythymidine, 3'-deoxyadenosine, 3'-deoxycytidine, 3'-deoxyinosine, 3'-deoxyguanosine, 3'-deoxythymidine).

In another example, therapeutic compounds that can act in conjunction with the oncolytic virus and/or adoptive T cell immunotherapy to decrease the proliferation, toxicity or cell killing properties of an oncolytic virus and/or adoptive T cell immunotherapy are compounds that can inhibit viral and/or adoptive T lymphocyte replication, inhibit viral and/or T lymphocyte toxins or cause viral and/or T lymphocyte death. A therapeutic compound that can inhibit viral and/or T lymphocyte replication, inhibit viral and/or T lymphocyte toxins, or cause viral and/or T lymphocyte death can generally include a compound that can block one or more steps in the viral and/or T lymphocyte life cycle, including, but not limited to, compounds that can inhibit viral and/or T lymphocyte DNA replication, viral and/or T lymphocyte RNA transcription, viral coat protein assembly, outer membrane or polysaccharide assembly. Any of a variety of compounds that can block one or more steps in a viral and/or adoptive T lymphocyte life cycle are known in the art, including any known antiviral compound (e.g., cidofovir), viral DNA polymerase inhibitors, viral RNA polymerase inhibitors, inhibitors of proteins that regulate viral DNA replication or RNA transcription.

In addition to combination therapy between chemotherapeutic agents and a oncolytic virus and/or adoptive T cell therapy provided herein, other more complex combination therapy strategies could be applied as well. For example, a combination therapy can include chemotherapeutic agents, therapeutic antibodies, and an oncolytic virus and/or adoptive T cell immunotherapy provided herein. Alternatively, another combination therapy can be the combination of radiation, therapeutic antibodies, and an oncolytic virus and/or adoptive T cell immunotherapy provided herein. Therefore, the concept of combination therapy also can be based on the application of an oncolytic virus and/or adoptive T cell immunotherapy provided herein along with one or more of the following therapeutic modalities, namely, chemotherapeutic agents, radiation therapy, therapeutic antibodies, hyper- or hypothermia therapy, siRNA, diagnostic/therapeutic bacteria, diagnostic/therapeutic mammalian cells, immunotherapy (including immunomodulatory compounds), and/or targeted toxins (delivered by antibodies, liposomes and nanoparticles).

Many cancers are treated with radiation therapy either as a primary therapeutic intervention or as a method for eliminating cancer cells remaining at sites of surgical cancer removal. The wide use of radiation treatment stems from the ability of gamma-irradiation to induce irreversible damage in targeted cells. Ionizing radiation triggers apoptosis, the intrinsic cellular death machinery in cancer cells, and the activation of apoptosis seems to be the principal mode by which cancer cells die following exposure to ionizing radiation. Low dose radiation enhances oncolytic virus colonization of cancers and metastases and has immunostimulatory effects on cancer tissue, thereby enhancing the cancer cell killing abilities of adoptively transferred cancer neoantigen-specific effector T lymphocytes.

For combination therapies with chemotherapeutic compounds, dosages for the administration of such compounds are known in the art or can be determined by one skilled in the art according to known clinical factors (e.g., subject's species, size, body surface area, age, sex, immune competence, and general health, duration and route of administration, the kind and stage of the disease, for example, cancer size, and other oncolytic viruses, treatments, or compounds, such as other chemotherapeutic drugs, being administered concurrently). In addition to the above factors, such levels can be affected by the infectivity of the oncolytic virus, and the nature of the oncolytic virus and/or adoptive T cell immunotherapy, as can be determined by one skilled in the art.

As will be understood by one of skill in the art, the optimal treatment regimen will vary and it is within the scope of the treatment methods to evaluate the status of the disease under treatment and the general health of the patient prior to, and following one or more cycles of combination therapy in order to determine the optimal therapeutic combination.

Therapeutic compounds also include, but are not limited to, compounds that exert an immunotherapeutic effect, stimulate or suppress the immune system, carry a therapeutic compound, or a combination thereof. Optionally, the therapeutic agent can exhibit or manifest additional properties, such as, properties that permit its use as an imaging agent, as described elsewhere herein. Such therapeutic compounds include, but are not limited to, anti-cancer antibodies, radiation therapy, siRNA molecules and compounds that suppress the immune system (i.e. immunosuppressors, immunosuppressive agents) or compounds that stimulate the immune system (i.e., immuno-modulators, including but not limited to, checkpoint inhibitors and co-stimulatory molecule agonists). In some cases, it is desirable to administer an immunosuppressive agent to a subject to suppress the immune system prior to the administration of the oncolytic virus and/or adoptive T cell immunotherapy in order to minimize any adverse reactions to the oncolytic virus and/or adoptive T cell immunotherapy. Exemplary immunosuppressive agents include, but are not limited to, glucocorticoids, alkylating agents, antimetabolites, and immunosuppressive antibodies.

Immunotherapy also includes for example, immunestimulating molecules (protein-based or non-protein-based), cells and antibodies. Immunotherapy treatments can include stimulating immune cells to act more effectively or to make the cancer cells or cancer-associated antigens recognizable to the immune system (i.e., break tolerance).

Cytokines and growth factors include, but are not limited to, interleukins, such as, for example, interleukin-1, interleukin-2, interleukin-6 and interleukin-7, interleukin-12, interleukin-21, tumor necrosis factors, such as tumor necrosis factor alpha (TNF-α), interferons such as interferon gamma (IFN-γ), granulocyte macrophage colony stimulating factors (GM-CSF), angiogenins, and tissue factors. Immune checkpoint modulators and immunostimulators include compounds that bind to proteins on T lymphocytes or other cells (such as cancer cells, antigen-presenting cells, macrophages, dendritic cells, MSDCs, or NK cells) or ligands thereof, which results in the modulation of effector T lymphocyte activity. Immunological targets that bind such compounds include, but are not limited to CTLA4, CD28, CD80 (B7-1), CD86 (B7-2), PD-1, PD-L1 (B7-H1), PD-L2 (B7-DC), 4-1BB (CD137/TNFRSF9), 4-1BB ligand, OX40 (CD134/TNFRSF4), OX40 ligand (CD252/TNFSF4) ICOS, ICOS ligand, GITR (CD357/TNFRSF18), GITR ligand (TNFSF18), CD27, CD70, TNFRSF25 (DR3), TL1A (TNFSF15), CD40 (TNFRSF5), CD40L (TNFSF5) HVEM (TNFRSF14), CD160, LIGHT (HVEML/TNFSF14), BTLA, Siglecs, LAG3, TIM3 (HAVCR2), Phosphatidylserine, galectins, B7-H3 (CD276), B7-H4 (VTCN1), VISTA, HHLA2, TMIGD2, Butyrophilin-like proteins, BTNL2, TIGIT, CD155 (PVR), CD226 (DNAM1), CD96, CD112 (PVRL2/nectin2), CD113 (PVRL3/nectin3), nectins CD25, CD30, VEGF, VEGFR, Neuropilin, IDO, TGF□, CD39, CD73, Adenosine, ADORA2A (A2A), IL-10, IL-27, CXCR4, CXCL12 KIRs (e.g., KIR2DL1, KIR2DL2, KIR2DL3), C-type lectins (e.g., NKG2A, NKG2D), MICA, MICB, ILT/LIR protein family members, CD244, CD48 CSF1R, SIRPA (CD172a), CD47 and TLRs (e.g. TLR1-11). Immune checkpoint modulators and immunostimulatory compounds include, but are not limited to, Ipilimumab, Tremelimumab, Galiximab, TGN1412, Pembrolizumab (MK-3475, Lambrolizumab), Nivolumab (ONO-4538, MDX1106, BMS936558), Atezolizumab (MPDL3280A), MEDI4736, Avelumab (MSB0010718C), PDR001, Pidilizumab (CT-011), MEDI0680 (AMP-514), AUNP-12, BMS-936559 (MDX1105), Urelumab, PF-05082566, BMS-663513, MEDI6383, MEDI6469, MOXR0916, GSK3174998, GSK3359609, TRX518, Varlilumab (CDX1127), CP-870893, BMS-986016, IMP321, Bavituximab, MGA271, Bevacizumab, MNRP1685A, INCB024360, Galunisertib, Ulocuplumab, BKT140, Larilumab, IPH2101, IPH2201, Emactuzumab (RG7155), CC-90002 and TLR agonists.

Anti-cancer antibodies include, but are not limited to, 3F8, 8H9, Abagovomab, Abituzumab, Adecatumumab, Afutuzumab, Alacizumab pegol, Altumomab pentetate, Amatuximab, Anatumomab mafenatox, Anetumab ravtansine, Apolizumab, Arcitumomab, Ascrinvacumab, Atezolizumab, Bavituximab, Bectumomab, Belimumab, Bevacizumab, Bivatuzumab mertansine, Blinatumomab, Brentuximab vedotin, Cantuzumab mertansine, Cantuzumab ravtansine, Capromab pendetide, Carlumab, Catumaxomab, cBR96-doxorubicin immunoconjugate, Cetuximab, Citatuzumab bogatox, Cixutumumab, Clivatuzumab tetraxetan, Codrituzumab, Coltuximab ravtansine, Conatumumab, Dacetuzumab, Dalotuzumab, Daratumumab, Demcizumab, Denintuzumab mafodotin, Derlotuximab biotin, Detumomab, Drozitumab, Durvalumab, Dusigitumab, Ecromeximab, Edrecolomab, Elgemtumab, Elotuzumab, Emactuzumab, Emibetuzumab, Enavatuzumab, Enfortumab vedotin, Enoblituzumab, Ensituximab, Epratuzumab, Ertumaxomab, Etaracizumab, Farletuzumab, FBTA05, Ficlatuzumab, Figitumumab, Flanvotumab, Galiximab, Ganitumab, Gemtuzumab ozogamicin, Girentuximab, Glembatumumab vedotin, Ibritumomab tiuxetan, Icrucumab, Igovomab, IMAB362, Imalumab, Imgatuzumab, Indatuximab ravtansine, Indusatumab vedotin, Inotuzumab ozogamicin, Intetumumab, Ipilimumab, Iratumumab, Isatuximab, Labetuzumab, Lambrolizumab, Lexatumumab, Lifastuzumab vedotin, Lilotomab satetraxetan, Lintuzumab, Lorvotuzumab mertansine, Lucatumumab, Lumiliximab, Lumretuzumab, Mapatumumab, Margetuximab, Matuzumab, Milatuzumab, Minretumomab, Mirvetuximab soravtansine, Mogamulizumab, Moxetumomab pasudotox, Nacolomab tafenatox, Naptumomab estafenatox, Narnatumab, Necitumumab, Nesvacumab, Nimotuzumab, Nivolumab, Nofetumomab merpentan, Obinutuzumab, Ocaratuzumab, Ofatumumab, Olaratumab, Onartuzumab, Ontuxizumab, Oportuzumab monatox, Oregovomab, Otlertuzumab, Panitumumab, Pankomab, Parsatuzumab, Pasotuxizumab, Patritumab, Pembrolizumab, Pemtumomab, Pertuzumab, Pidilizumab, Pinatuzumab vedotin, Polatuzumab vedotin, Pritumumab, Racotumomab, Radretumab, Ramucirumab, Rilotumumab, Rituximab, Robatumumab, Sacituzumab govitecan, Samalizumab, Satumomab pendetide, Seribantumab, SGN-CD19A, SGN-CD33A, Sibrotuzumab, Siltuximab, Sofituzumab vedotin, Tabalumab, Tacatuzumab tetraxetan, Taplitumomab paptox, Tarextumab, Tenatumomab, Teprotumumab, Tetulomab, TGN1412, Ticilimumab (=tremelimumab), Tigatuzumab, TNX-650, Tovetumab, Trastuzumab, Trastuzumab emtansine, TRBS07, Tremelimumab, Tucotuzumab celmoleukin, Ublituximab, Urelumab, Vandortuzumab vedotin, Vantictumab, Vanucizumab, Veltuzumab, Volociximab, Vorsetuzumab mafodotin, Votumumab, Zalutumumab, and Zatuximab.

Thus, provided herein are methods of administering to a subject one or more immuno-modulating/therapeutic compounds that can act in conjunction with the oncolytic virus and/or adoptive T cell immunotherapy to stimulate or enhance the immune system, thereby enhancing the effect of the oncolytic virus and/or adoptive T cell immunotherapy. Such immunotherapy can be either delivered as a separate therapeutic modality or could be encoded (if the immunotherapy is protein-based) by the administered oncolytic virus and/or adoptive T cell immunotherapy.

Biological therapies are treatments that use natural body substances or drugs made from natural body substances. They can help to treat a cancer and control side effects caused by other cancer treatments such as chemotherapy. Biological therapies are also sometimes called Biological Response Modifiers (BRM's), biologic agents or simply "biologics" because they stimulate the body to respond biologically (or naturally) to cancer. Immunotherapy is treatment using natural substances that the body uses to fight infection and disease. Because it uses natural substances, immunotherapy is also a biological therapy. There are several types of drugs that come under the term biological therapy: these include, for example, monoclonal antibodies, cancer vaccines, growth factors, cancer growth inhibitors, anti-angiogenic factors, interferon alpha, interleukin-2, gene therapy and BCG vaccine.

Monoclonal antibodies are of particular interest for treating cancer because of the specificity of binding to a unique antigen and the ability to produce large quantities of the agent in the laboratory for mass distribution. Monoclonal antibodies can be engineered to act in the same way as immune system proteins: that is, to seek out and kill foreign matter in the body, such as viruses. Monoclonal antibodies can be designed to recognize epitopes on the surface of cancer cells. The antibodies target specifically bind to the epitopes and either kill the cancer cells or deliver a therapeutic agent to the cancer cell. Methods of conjugating therapeutic agents to antibodies are well-known in the art. Different antibodies have to be made for different types of cancer; for example, Rituximab recognizes CD20 protein on the outside of non-Hodgkin's lymphoma cells; ADEPT is a treatment using antibodies that recognize bowel (colon) cancer; and Trastuzumab (Herceptin) recognizes breast cancer cells that produce too much of the protein HER 2 ("HER 2 positive"). Other antibodies include, for example, 3F8, 8H9, Abagovomab, Abituzumab, Adecatumumab, Afutuzumab, Alacizumab pegol, Altumomab pentetate, Amatuximab, Anatumomab mafenatox, Anetumab ravtansine, Apolizumab, Arcitumomab, Ascrinvacumab, Atezolizumab, Bavituximab, Bectumomab, Belimumab, Bevacizumab, Bivatuzumab mertansine, Blinatumomab, Brentuximab vedotin, Cantuzumab mertansine, Cantuzumab ravtansine, Capromab pendetide, Carlumab, Catumaxomab, cBR96-doxorubicin immunoconjugate, Cetuximab, Citatuzumab bogatox, Cixutumumab, Clivatuzumab tetraxetan, Codrituzumab, Coltuximab ravtansine, Conatumumab, Dacetuzumab, Dalotuzumab, Daratumumab, Demcizumab, Denintuzumab mafodotin, Derlotuximab biotin, Detumomab, Drozitumab, Durvalumab, Dusigitumab, Ecromeximab, Edrecolomab, Elgemtumab, Elotuzumab, Emactuzumab, Emibetuzumab, Enavatuzumab, Enfortumab vedotin, Enoblituzumab, Ensituximab, Epratuzumab, Ertumaxomab, Etaracizumab, Farletuzumab, FBTA05, Ficlatuzumab, Figitumumab, Flanvotumab, Galiximab, Ganitumab, Gemtuzumab ozogamicin, Girentuximab, Glembatumumab vedotin, Ibritumomab tiuxetan, Icrucumab, Igovomab, IMAB362, Imalumab, Imgatuzumab, Indatuximab ravtansine, Indusatumab vedotin, Inotuzumab ozogamicin, Intetumumab, Ipilimumab, Iratumumab, Isatuximab, Labetuzumab, Lambrolizumab, Lexatumumab, Lifastuzumab vedotin, Lilotomab satetraxetan, Lintuzumab, Lorvotuzumab mertansine, Lucatumumab, Lumiliximab, Lumretuzumab, Mapatumumab, Margetuximab, Matuzumab, Milatuzumab, Minretumomab, Mirvetuximab soravtansine, Mogamulizumab, Moxetumomab pasudotox, Nacolomab tafenatox, Naptumomab estafenatox, Narnatumab, Necitumumab, Nesvacumab, Nimotuzumab, Nivolumab, Nofetumomab merpentan, Obinutuzumab, Ocaratuzumab, Ofatumumab, Olaratumab, Onartuzumab, Ontuxizumab, Oportuzumab monatox, Oregovomab, Otlertuzumab, Panitumumab, Pankomab, Parsatuzumab, Pasotuxizumab, Patritumab, Pembrolizumab, Pemtumomab, Pertuzumab, Pidilizumab, Pinatuzumab vedotin, Polatuzumab vedotin, Pritumumab, Racotumomab, Radretumab, Ramucirumab, Rilotumumab, Robatumumab, Sacituzumab govitecan, Samalizumab, Satumomab pendetide, Seribantumab, SGN-CD19A, SGN-CD33A, Sibrotuzumab, Siltuximab, Sofituzumab vedotin, Tabalumab, Tacatuzumab tetraxetan, Taplitumomab paptox, Tarextumab, Tenatumomab, Teprotumumab, Tetulomab, TGN1412, Ticilimumab (=tremelimumab), Tigatuzumab, TNX-650, Tovetumab, Trastuzumab emtansine, TRBS07, Tremelimumab, Tucotuzumab celmoleukin, Ublituximab, Urelumab, Vandortuzumab vedotin, Vantictumab, Vanucizumab, Veltuzumab, Volociximab, Vorsetuzumab mafodotin, Votumumab, Zalutumumab, and Zatuximab. Thus, the oncolytic viruses and/or adoptive cell immunotherapy provided herein can be administered concurrently with, or sequentially to, one or more monoclonal antibodies in the treatment of cancer. In one example, additional therapy is administered in the form of one or more of any of the other treatment modalities provided herein.

Growth factors are natural substances that can for example stimulate the bone marrow to make blood cells. Recombinant technology can be used to generate growth factors which can be administered to a subject to increase the number of white blood cells, red blood cells and stem cells in the blood. Growth factors used in cancer treatment to boost white blood cells include granulocyte colony stimulating factor (G-CSF) also called filgrastim (Neupogen) or lenograstim (Granocyte) and GM-CSF, also called molgramostim or sargramostim (Leukine). Thus, the oncolytic viruses and/or adoptive T cell therapy provided herein can be administered concurrently with, or sequentially to, a growth factor such as GM-CSF, interleukin 2, interleukin 7, interleukin 15 and/or interleukin 21, in the treatment of cancer.

Cancer growth inhibitors use cell-signaling molecules which control the growth and multiplication of cells, such as cancer cells. Drugs that block these signaling molecules can stop cancers from growing and dividing. Cancer growth factors include, but are not limited to, tyrosine kinases. Thus, drugs that block tyrosine kinases are tyrosine kinase inhibitors (TKIs). Examples of TKIs include, but are not limited to, Erlotinib (Tarceva, OSI—774), Iressa (Gefitinib, ZD 1839) and Imatinib (Glivec, STI 571). Another type of growth inhibitor is Bortezomib (Velcade) for multiple myeloma and for some other cancers. Velcade is a proteasome inhibitor. Proteasomes are found in all cells and help break down proteins in cells. Interfering with the action of proteasomes causes a buildup of proteins in the cell to toxic levels; thereby killing the cancer cells. Cancer cells are more sensitive to Velcade than normal cells. Thus, the oncolytic viruses and/or adoptive T cell immunotherapy provided herein can be administered concurrently with, or sequentially to, a cancer growth inhibitor, such as Velcade, in the treatment of cancer.

Cancers need a blood supply to expand and grow their own blood vessels as they get bigger. Without its own blood supply, a cancer cannot grow due to lack of nutrients and oxygen. Anti-angiogenic drugs stop cancers from developing their own blood vessels. Examples of these types of drugs include, but are not limited to, Thalidomide, mainly for treating myeloma but also in trials for other types of cancer, and Bevacizumab (Avastin). Thus, the oncolytic viruses and/or adoptive T cell immunotherapy provided herein can be administered concurrently with, or sequentially to, an anti-angiogenic drug in the treatment of cancer.

Interferon-alpha (IFN-α) is a natural substance produced in the body, in very small amounts, as part of the immune response. IFN-α is administered as a treatment to boost the immune system and help fight cancers such as renal cell (kidney) cancer, malignant melanoma, multiple myeloma and some types of leukemias. IFN-α works in several ways: it can help to stop cancer cells growing, it can also boost the immune system to help it attack the cancer, and it can affect the blood supply to the cancer cells. Thus, the oncolytic viruses and/or adoptive T cell immunotherapy provided herein can be administered concurrently with, or sequentially to, IFN-α in the treatment of cancer.

Gene therapy involves treating cancer by blocking abnormal genes in cancer cells, repairing or replacing abnormal genes in cancer cells, encouraging even more genes to become abnormal in cancer cells so that they die or become sensitive to treatment, using oncolytic viruses to carry treatment-activating enzymes into the cancer cells, or combination thereof. As a result, cancer cells die due to damage in the cell. Cancer cells develop as a result of several types of mutations in several of their genes. Targeted genes include, but are not limited to, those that encourage the cell to multiply (i.e., oncogenes), genes that stop the cell multiplying (i.e., cancer suppressor genes) and genes that repair other damaged genes. Gene therapy can involve repair of damaged oncogenes or blocking the proteins that the oncogenes produce. The cancer suppressor gene, p53, is damaged in many human cancers. Oncolytic viruses have been used in to deliver an undamaged p53 gene into cancer cells, and early clinical trials are now in progress looking at treating cancers with modified p53-producing oncolytic viruses. Gene therapy could be used to replace the damaged DNA repairing genes. In an alternative example, methods of increasing DNA damage within a cancer cell can promote death of the cancer cell or cause increased susceptibility of the cancer cell to other cancer treatments, such as radiotherapy or chemotherapy. Thus, the oncolytic viruses and/or adoptive T cell immunotherapy provided herein can be administered concurrently with, or sequentially to, any of the gene therapy methods provided herein or known in the art in the treatment of cancer.

The gene product or therapeutic agent could be given as a separate modality, i.e., not necessarily to be encoded or carried by the oncolytic virus and/or the adoptive T cell immunotherapy. This can be give prior to, concurrently, or after oncolytic virus and/or adoptive T cell immunotherapy treatment.

Effective delivery of each component of the combination therapy is an important aspect of the methods provided herein. In accordance with one aspect, the modes of administration discussed below exploit one or more of the key features: (i) delivery of an oncolytic virus and/or adoptive T cell immunotherapy provided herein to the cancers by a mode of administration designed to achieve highest titer of oncolytic virus and/or adoptively transferred T cells and greatest therapeutic effect; (ii) delivery of any other mentioned therapeutic modalities to the cancer by a mode of administration to achieve the optimal therapeutic effect. The dose scheme of the combination therapy administered is such that the combination of the two or more therapeutic modalities is therapeutically effective. Dosages will vary in accordance with such factors as the age, health, sex, size and weight of the patient, the route of administration, the toxicity of the drugs, frequency of treatment and the relative susceptibilities of the cancer to each of the therapeutic modalities.

10. REFERENCES

1. Mahoney K M, Rennert P D, Freeman G J (2015) Combination cancer immunotherapy and new immunomodulatory targets. Nat Rev Drug Discov 14: 561-584.
2. Sanmamed M F, Pastor F, Rodriguez A, Perez-Gracia J L, Rodriguez-Ruiz M E, Jure-Kunkel M, et al. (2015) Agonists of Co-stimulation in Cancer Immunotherapy Directed Against CD137, OX40, GITR, CD27, CD28, and ICOS. Semin Oncol 42: 640-655.
3. Besser M J, Shapira-Frommer R, Treves A J, Zippel D, Itzhaki O, Hershkovitz L, et al. (2010) Clinical responses in a phase I I study using adoptive transfer of short-term cultured tumor infiltration lymphocytes in metastatic melanoma patients. Clin Cancer Res 16: 2646-2655.
4. Cerullo V, Diaconu I, Kangasniemi L, Rajecki M, Escutenaire S, Koski A, et al. (2011) Immunological effects of low-dose cyclophosphamide in cancer patients treated with oncolytic adenovirus. Mol Ther 19: 1737-1746.
5. Chang A E, Aruga A, Cameron M J, Sondak V K, Normolle D P, Fox B A, et al. (1997) Adoptive immunotherapy with vaccine-primed lymph node cells secondarily activated with anti-CD3 and interleukin-2. J Clin Oncol 15: 796-807.
6. Chang A E, Li Q, Jiang G, Sayre D M, Braun T M, Redman B G (2003) Phase I I trial of autologous tumor vaccination, anti-CD3-activated vaccine-primed lymphocytes, and interleukin-2 in stage I V renal cell cancer. J Clin Oncol 21: 884-890.
7. Dudley M E, Wunderlich J R, Yang J C, Sherry R M, Topalian S L, Restifo N P, et al. (2005) Adoptive cell transfer therapy following non-myeloablative but lymphodepleting chemotherapy for the treatment of patients with refractory metastatic melanoma. J Clin Oncol 23: 2346-2357.
8. Dudley M E, Yang J C, Sherry R, Hughes M S, Royal R, Kammula U, et al. (2008) Adoptive cell therapy for patients with metastatic melanoma: evaluation of intensive myeloablative chemoradiation preparative regimens. J Clin Oncol26: 5233-5239.
9. Pilon-Thomas S, Kuhn L, Ellwanger S, Janssen W, Royster E, Marzban S, et al. (2012) Efficacy of adoptive cell transfer of tumor-infiltrating lymphocytes after lymphopenia induction for metastatic melanoma. J Immunother 35: 615-620.
10. Radvanyi L G, Bernatchez C, Zhang M, Fox P S, Miller P, Chacon J, et al. (2012) Specific lymphocyte subsets predict response to adoptive cell therapy using expanded autologous tumor-infiltrating lymphocytes in metastatic melanoma patients. Clin Cancer Res 18: 6758-6770.
11. Sloan A E, Dansey R, Zamorano L, Barger G, Hamm C, Diaz F, et al. (2000) Adoptive immunotherapy in patients with recurrent malignant glioma: preliminary results of using autologous whole-tumor vaccine plus granulocyte-macrophage colony-stimulating factor and adoptive transfer of anti-CD3-activated lymphocytes. Neurosurg Focus 9: e9.
12. Wood G W, Holladay F P, Turner T, Wang Y Y, Chiga M (2000) A pilot study of autologous cancer cell vaccination and cellular immunotherapy using anti-CD3 stimulated lymphocytes in patients with recurrent grade III/I V astrocytoma. J Neurooncol 48: 113-120.
13. Gentschev I, Donat U, Hofmann E, Weibel S, Adelfinger M, Raab V, et al. (2010) Regression of human prostate tumors and metastases in nude mice following treatment with the recombinant oncolytic vaccinia virus GLV-1h68. J Biomed Biotechnol 2010: 489759.
14. Gentschev I, Ehrig K, Donat U, Hess M, Rudolph S, Chen N, et al. (2010) Significant Growth Inhibition of Canine Mammary Carcinoma Xenografts following Treatment with Oncolytic Vaccinia Virus GLV-1h68. J Oncol 2010: 736907.
15. Gentschev I, Muller M, Adelfinger M, Weibel S, Grummt F, Zimmermann M, et al. (2011) Efficient colonization and therapy of human hepatocellular carcinoma (HCC) using the oncolytic vaccinia virus strain GLV-1h68. PLoS One 6: e22069.
16. Gujar S A, Lee P W (2014) Oncolytic virus-mediated reversal of impaired tumor antigen presentation. Front Oncol 4: 77.
17. Kawai T, Akira S (2009) The roles of TLRs, RLRs and NLRs in pathogen recognition. Int Immunol 21: 317-337.
18. Kawai T, Akira S (2010) The role of pattern-recognition receptors in innate immunity: update on Toll-like receptors. Nat Immunol 11: 373-384.
19. Kawai T, Akira S (2011) Toll-like receptors and their crosstalk with other innate receptors in infection and immunity. Immunity 34: 637-650.
20. Shmulevitz M, Lee P W (2012) Exploring host factors that impact reovirus replication, dissemination, and reovirus-induced cell death in cancer versus normal cells in culture. Methods Mol Biol 797: 163-176.
21. Benencia F, Courreges M C, Fraser N W, Coukos G (2008) Herpes virus oncolytic therapy reverses tumor immune dysfunction and facilitates tumor antigen presentation. Cancer Biol Ther 7: 1194-1205.
22. Errington F, Steele L, Prestwich R, Harrington K J, Pandha H S, Vidal L, et al. (2008) Reovirus activates human dendritic cells to promote innate antitumor immunity. J Immunol 180: 6018-6026.
23. Fonteneau J F, Guillerme J B, Tangy F, Gregoire M (2013) Attenuated measles virus used as an oncolytic virus activates myeloid and plasmacytoid dendritic cells. Oncoimmunology 2: e24212.
24. Greiner S, Humrich J Y, Thuman P, Sauter B, Schuler G, Jenne L (2006) The highly attenuated vaccinia virus strain modified virus Ankara induces apoptosis in melanoma cells and allows bystander dendritic cells to generate a potent anti-tumoral immunity. Clin Exp Immunol 146: 344-353.
25. Gujar S A, Marcato P, Pan D, Lee P W (2010) Reovirus virotherapy overrides tumor antigen presentation evasion and promotes protective antitumor immunity. Mol Cancer Ther 9: 2924-2933.
26. Hervas-Stubbs S, Perez-Gracia J L, Rouzaut A, Sanmamed M F, Le Bon A, Melero I (2011) Direct effects of type I interferons on cells of the immune system. Clin Cancer Res 17: 2619-2627.
27. Montoya M, Schiavoni G, Mattei F, Gresser I, Belardelli F, Borrow P, et al. (2002) Type I interferons produced by dendritic cells promote their phenotypic and functional activation. Blood 99: 3263-3271.
28. Rudd B D, Luker G D, Luker K E, Peebles R S, Lukacs N W (2007) Type I interferon regulates respiratory virus infected dendritic cell maturation and cytokine production. Viral Immunol 20: 531-540.
29. Kawai T, Akira S (2006) Innate immune recognition of viral infection. Nat Immunol 7: 131-137.
30. Heo J, Breitbach C J, Moon A, Kim C W, Patt R, Kim M K, et al. (2011) Sequential therapy with JX-594, a targeted oncolytic poxvirus, followed by sorafenib in hepatocellular carcinoma: preclinical and clinical demonstration of combination efficacy. Mol Ther 19: 1170-1179.
31. Liu T C, Hwang T, Park B H, Bell J, Kim D H (2008) The targeted oncolytic poxvirus JX-594 demonstrates antitumoral, antivascular, and anti-HBV activities in patients with hepatocellular carcinoma. Mol Ther 16: 1637-1642.
32. Yu Y A, Shabahang S, Timiryasova T M, Zhang Q, Beltz R, Gentschev I, et al. (2004) Visualization of tumors and metastases in live animals with bacteria and vaccinia virus encoding light-emitting proteins. Nat Biotechnol 22: 313-320.
33. Zhang Q, Yu Y A, Wang E, Chen N, Danner R L, Munson P J, et al. (2007) Eradication of solid human breast tumors in nude mice with an intravenously injected light-emitting oncolytic vaccinia virus. Cancer Res 67: 10038-10046.
34. Dudley M E, Wunderlich J R, Robbins P F, Yang J C, Hwu P, Schwartzentruber D J, et al. (2002) Cancer regression and autoimmunity in patients after clonal repopulation with antitumor lymphocytes. Science 298: 850-854.
35. Liikanen I, Ahtiainen L, Hirvinen M L, Bramante S, Cerullo V, Nokisalmi P, et al. (2013) Oncolytic adenovirus with temozolomide induces autophagy and antitumor immune responses in cancer patients. Mol Ther 21: 1212-1223.
36. Bartlett D L, Liu Z, Sathaiah M, Ravindranathan R, Guo Z, He Y, et al. (2013) Oncolytic viruses as therapeutic cancer vaccines. Mol Cancer 12: 103.
37. Le D T, Jaffee E M (2012) Regulatory T-cell modulation using cyclophosphamide in vaccine approaches: a current perspective. Cancer Res 72: 3439-3444.

What is claimed and desired to be secured by Letters Patent is as follows:

1. A cancer immunotherapy method for treating cancer in a patient comprising:
vaccinating the patient with a vaccine comprised of the patient's own malignancy and an immunologic adjuvant;
isolating primed T lymphocytes from lymphoid tissue, peripheral blood or cancer tissue of the patient;
stimulating the primed T lymphocytes to differentiate into effector T lymphocytes in vitro;

stimulating the effector T lymphocytes to proliferate in vitro;
administering an oncolytic virus to the patient after said step of vaccinating the patient with a vaccine comprised of the patient's own malignancy; and
infusing the effector T lymphocytes back into the patient after said administering of the oncolytic virus step.

2. The method of claim 1, further comprising administering a booster vaccination comprising a first oncolytic virus after the vaccination step and prior to the isolating primed T lymphocytes step.

3. The method of claim 1, wherein the vaccinating step is preceded by administration of a first oncolytic virus within two weeks prior to the vaccinating step.

4. The method of claim 1, wherein the oncolytic virus is selected from the group consisting of vaccinia virus, reovirus, measles virus, mumps virus, adenovirus and herpes virus, vesicular stomatitis virus, newcastle disease virus, parvovirus, poliovirus, coxsackie virus, sindbis virus, seneca valley virus, maraba virus and combinations thereof.

5. The method of claim 1, wherein the cancer is selected from the group consisting of breast cancer, brain and central nervous system cancer, kidney cancer, lung cancer, and ovarian cancer.

6. The method of claim 1, further comprising after the infusing step, administering a second oncolytic virus to the patient.

7. The method of claim 1, further comprising before the vaccinating step, administering a first oncolytic virus to the patient, and then removing the patient's own malignancy.

8. The method of claim 1, further comprising before the vaccinating step, removing the patient's own malignancy and administering a first oncolytic virus to the patient, wherein administering the first oncolytic virus occurs simultaneously with or after the removing the patient's own malignancy.

9. The method of claim 1, further comprising before the vaccinating step, removing the patient's own malignancy, combining the patient's own malignancy with a first oncolytic virus and using the combined virus/malignancy in the vaccinating step.

10. The method of claim 1, wherein a second oncolytic virus is delivered by the effector T lymphocytes in the infusion step.

11. The method of claim 1, further comprising administering an immunomodulatory compound.

12. The method of claim 11, wherein the immunomodulatory compound is infused into the patient with the effector T lymphocytes, administered to the patient after the infusing step, administered to the patient after the vaccinating step and prior to the isolating primed T lymphocytes step, and/or delivered to the primed T lymphocytes between the isolating step and the infusing step.

13. The method of claim 12, wherein the immunomodulatory compound is delivered to the primed T lymphocytes during the differentiation step, the proliferation step, or both.

14. The method of claim 11, wherein the immunomodulatory compound is selected from the group consisting of compounds that bind to or otherwise interfere with the function of immune-inhibitory signaling molecules, agonistic compounds that activate or augment the immunostimulatory signaling molecules, and combinations thereof.

15. The method of claim 11, wherein the immunomodulatory compound is selected from the group consisting of genetically engineered or otherwise modified antibodies, natural ligands, small molecules, and combinations thereof.

16. The method of claim 1, wherein the oncolytic virus has been genetically engineered to include deletion of a gene encoded by the wild-type strain of the virus, wherein the genes encodes immune modifying gene product(s), metabolic gene product(s), or cell cycle controlling gene product(s).

17. The method of claim 1, wherein the oncolytic virus has been genetically engineered to encode a gene product selected from the group consisting of an anti-cancer agent, an anti-angiogenic agent, an immunomodulatory molecule or an antigen (e.g., cancer (neo)antigens, cancer-associated antigens, tissue-specific antigens, bacterial antigens, viral antigens, yeast antigens, fungal antigens, protozoan antigens, parasite antigens and mitogens), a hormone, a growth factor, a cytokine, a chemokine, a costimulatory molecule, a ribozyme, a transporter protein, a single chain antibody (e.g., an anti-VEGF or anti-VEGFR, or anti-EGFR antibody), an antibody (agonistic or antagonistic) against immune modulating proteins, an antisense or ds RNA or other RNA product, a prodrug converting enzyme, an siRNA, a microRNA, a toxin, an anti-cancer oligopeptide, a mitosis inhibitor protein, an antimitotic oligopeptide, an anti-cancer polypeptide antibiotic, an angiogenesis inhibitor, a cancer suppressor, a cytotoxic protein, a cytostatic protein, an enzyme that modifies a substrate to produce a detectable product or signal, an enzyme detectable by antibodies, a protein that can bind a contrasting agent.

18. The method of claim 1, wherein the administration of the oncolytic virus step proceeds the infusing step by one day up to two weeks prior to the infusing step.

19. The method of claim 1, wherein primed T lymphocytes are isolated from lymphoid tissue or peripheral blood of the patient.

* * * * *